United States Patent [19]
Yoon

[11] Patent Number: 5,807,402
[45] Date of Patent: Sep. 15, 1998

[54] SAFETY PENETRATING INSTRUMENT WITH PROTECTIVE SHEATH, TRIGGERED PENETRATING MEMBER RETRACTION AND SINGLE AND SAFETY MEMBER PROTRUSION

[76] Inventor: InBae Yoon, 2101 Highland Ridge Dr., Phoenix, Md. 21131

[21] Appl. No.: 889,167

[22] Filed: Jul. 7, 1997

Related U.S. Application Data

[60] Division of Ser. No. 279,170, Jul. 22, 1994, Pat. No. 5,645,556, which is a continuation-in-part of Ser. No. 83,220, Jun. 24, 1993, Pat. No. 5,431,635, Ser. No. 83,728, Jun. 29, 1993, Pat. No. 5,466,224, Ser. No. 115,152, Sep. 2, 1993, Pat. No. 5,578,053, and Ser. No. 177,616, Jan. 4, 1994, said Ser. No. 83,220, and Ser. No. 83,728, each is a continuation-in-part of Ser. No.628,899, Dec. 18, 1990, Pat. No. 5,226,426, and Ser. No. 817,113, Jan. 6, 1992, Pat. No. 5,350,393.

[51] Int. Cl.$^6$ ............................................. A61M 5/20
[52] U.S. Cl. ......................... 606/185; 604/165; 604/170
[58] Field of Search ..................... 606/167, 171, 606/185; 604/95, 158, 162, 163, 164, 165, 170, 272, 274, 280, 169; 128/751, 752, 753, 754

[56] References Cited

U.S. PATENT DOCUMENTS

| | | |
|---|---|---|
| Re. 32,922 | 5/1989 | Levin et al. . |
| 1,087,845 | 2/1914 | Stevens . |
| 1,213,001 | 1/1917 | Philips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,817,603 | 4/1989 | Turner et al. . |
| 4,820,275 | 4/1989 | Haber et al. . |
| 4,828,547 | 5/1989 | Sahi et al. . |
| 4,869,717 | 9/1989 | Adair . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9304632 | 3/1993 | WIPO . |
| 9304715 | 3/1993 | WIPO . |
| 9304716 | 3/1993 | WIPO . |
| 9317626 | 9/1993 | WIPO . |

*Primary Examiner*—Guy V. Tucker

[57] ABSTRACT

A safety penetrating instrument for establishing a portal in a wall of an anatomical cavity includes a cannula, a penetrating member disposed in the cannula, a protective sheath disposed between the penetrating member and the cannula to place the tip of the penetrating member in a protected, non-exposed state, and various mechanisms for simultaneously retracting one or both of the penetrating member and the protective sheath while extending the cannula. Retraction of one or both of the penetrating member and the protective sheath and extension or protrusion of the cannula is triggered individually or in combination by movement of one or more of the three members upon entering the anatomical cavity. Additionally, a probe can be carried by the safety penetrating instrument for triggering retraction and/or extension of the members in a similar manner or upon moving a predetermined proximal distance during penetration of the anatomical cavity wall.

13 Claims, 17 Drawing Sheets

U.S. PATENT DOCUMENTS

| | | |
|---|---|---|
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,129,885 | 7/1992 | Green et al. . |
| 5,152,754 | 10/1992 | Plyley et al. . |
| 5,158,552 | 10/1992 | Borgia et al. . |
| 5,207,647 | 5/1993 | Phelps . |
| 5,215,526 | 6/1993 | Deniega et al. . |
| 5,224,951 | 7/1993 | Freitas . |
| 5,224,952 | 7/1993 | Deniega et al. . |
| 5,226,426 | 7/1993 | Yoon . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 12/1993 | Deniega . |
| 5,275,583 | 1/1994 | Crainich . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen . |
| 5,350,393 | 9/1994 | Yoon . |
| 5,360,405 | 11/1994 | Yoon . |
| 5,364,372 | 11/1994 | Danks et al. . |
| 5,366,445 | 11/1994 | Haber et al. . |
| 5,368,607 | 11/1994 | Freitas . |
| 5,372,588 | 12/1994 | Farley et al. . |
| 5,374,252 | 12/1994 | Banks et al. . |
| 5,376,082 | 12/1994 | Phelps . |
| 5,380,288 | 1/1995 | Hart et al. . |
| 5,383,859 | 1/1995 | Sewell, Jr. . |

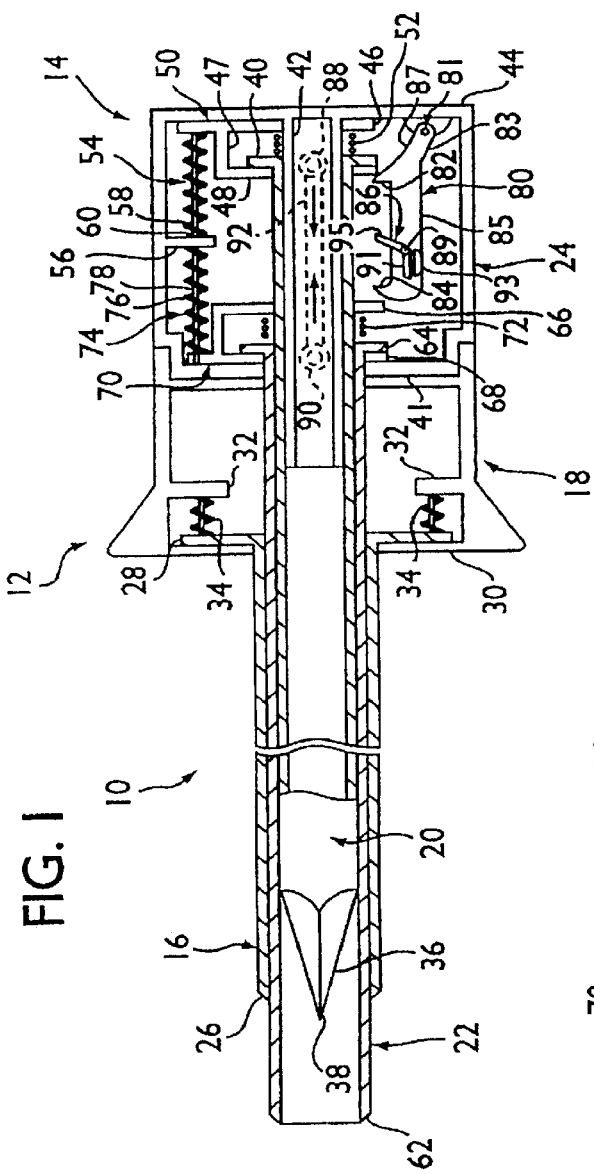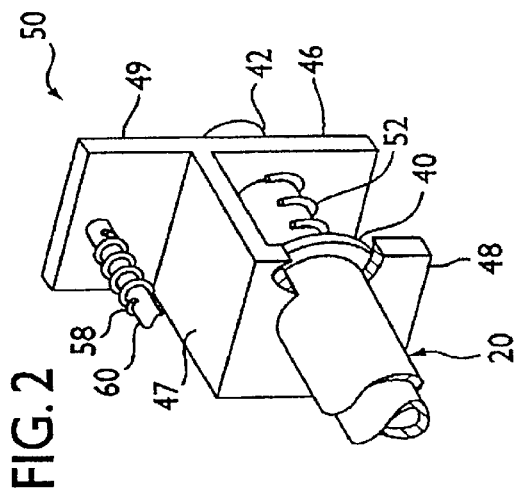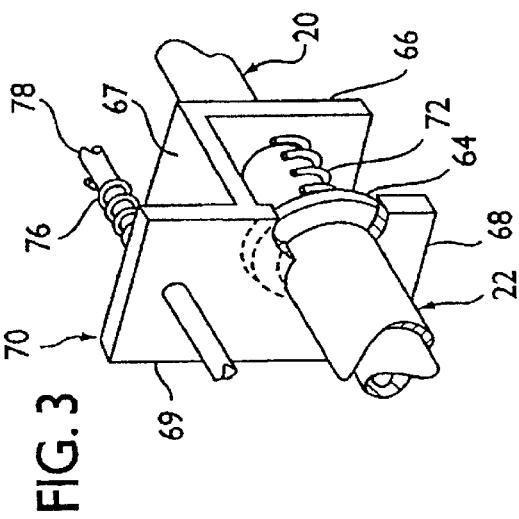

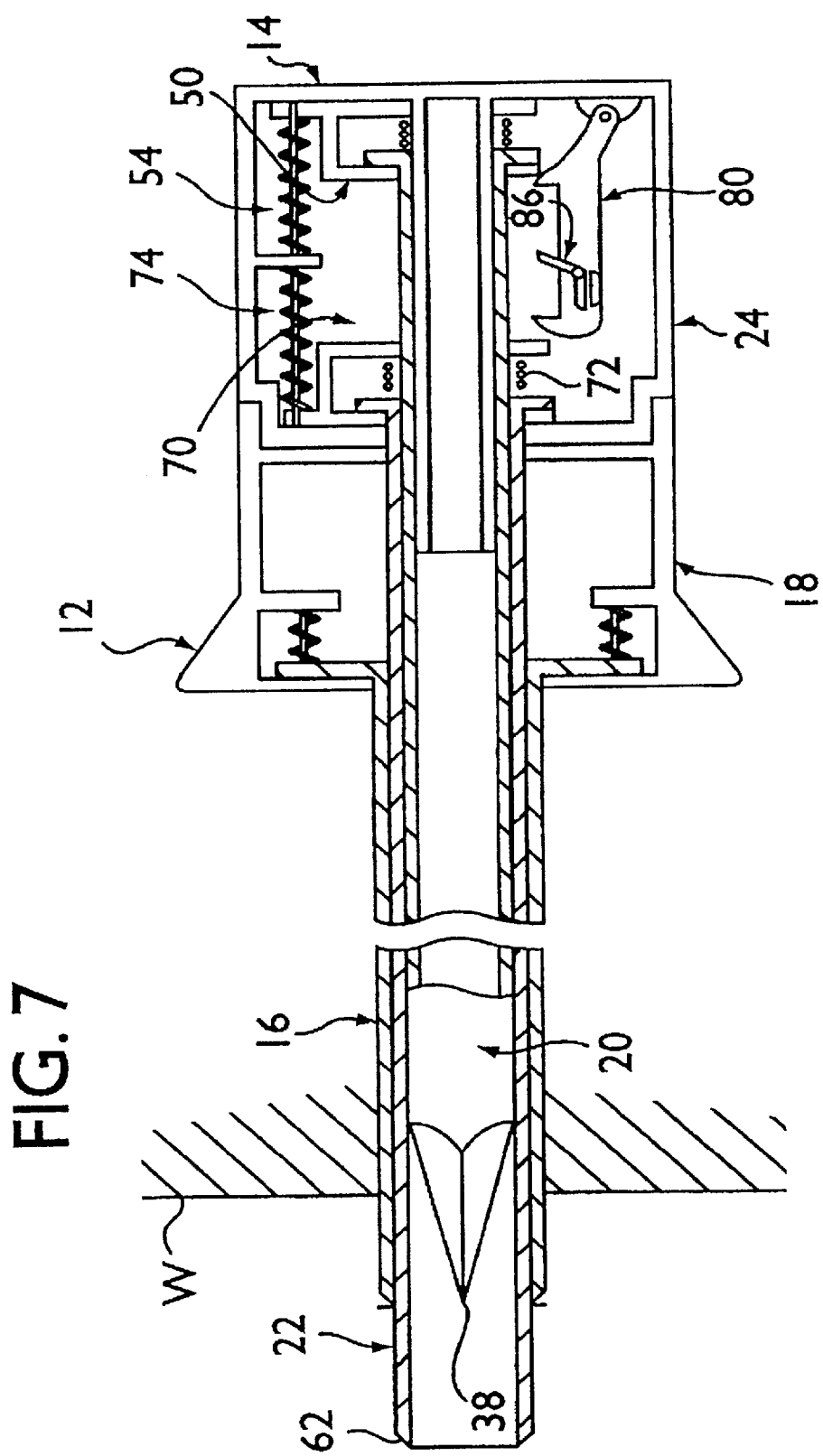

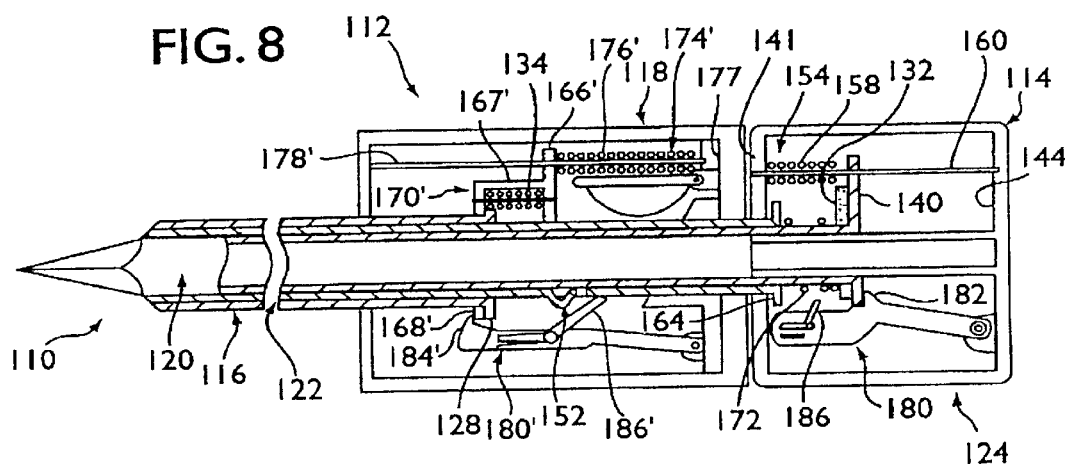
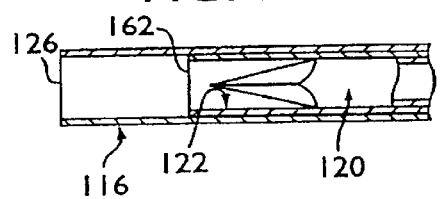
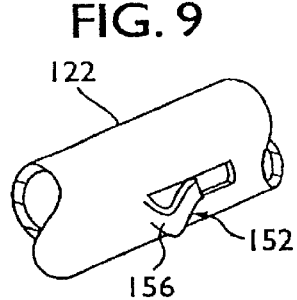
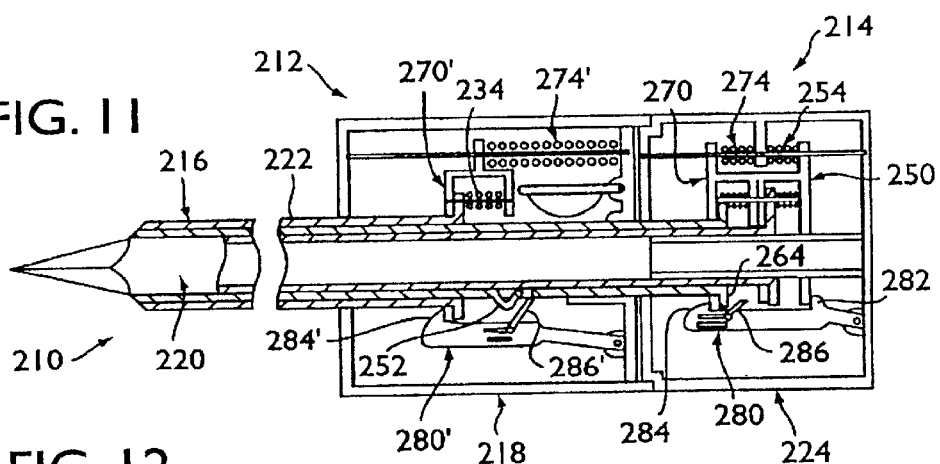
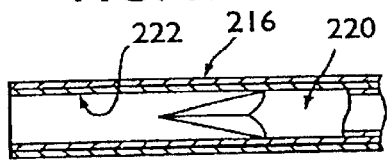

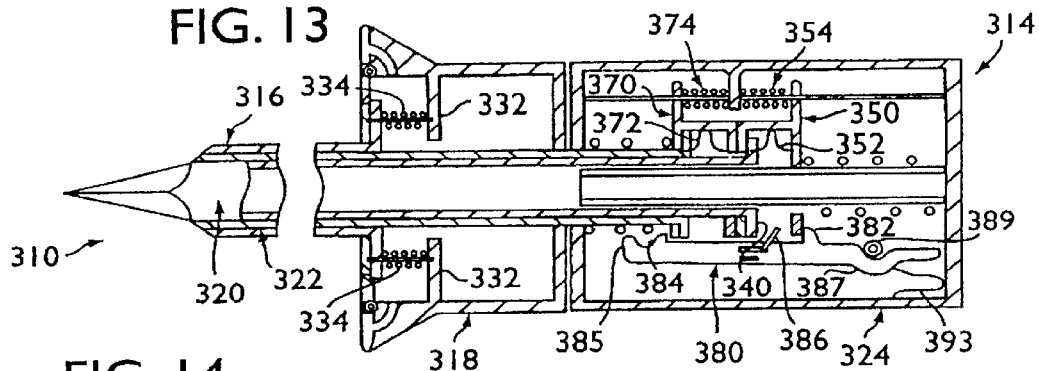
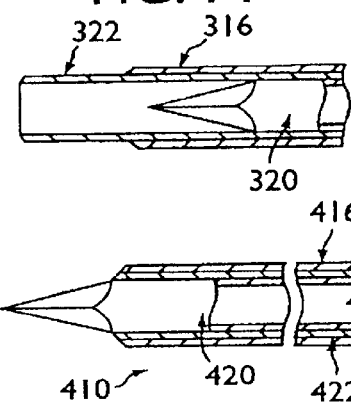
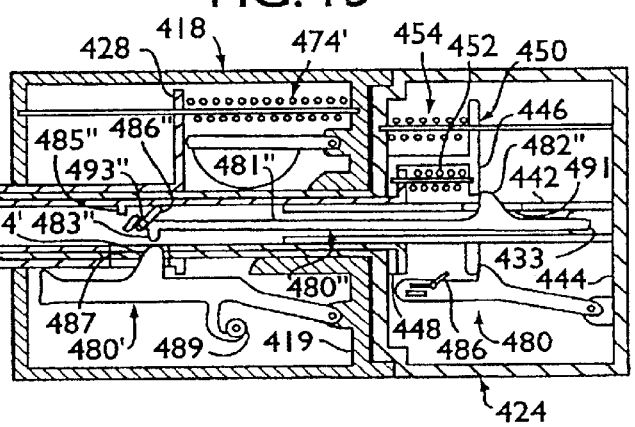
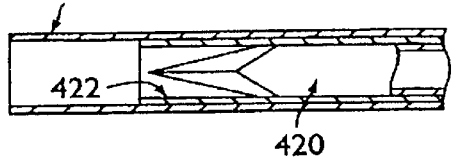
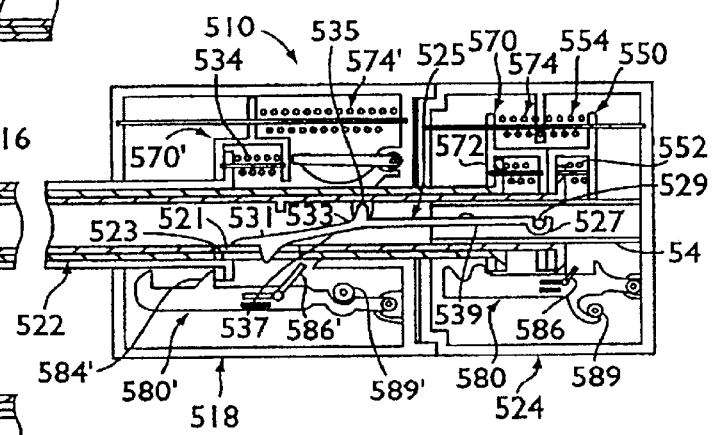
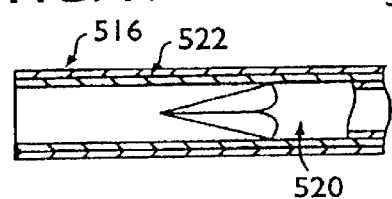

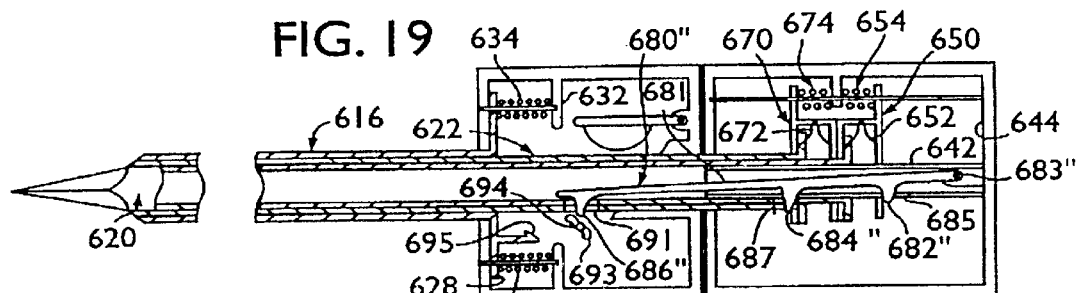
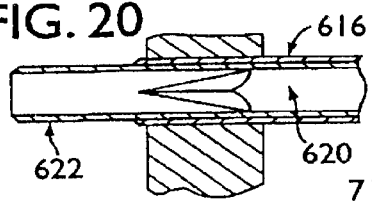
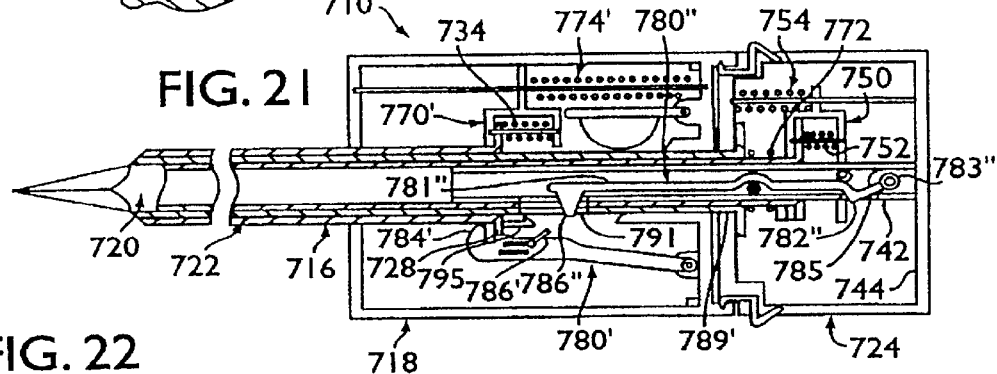
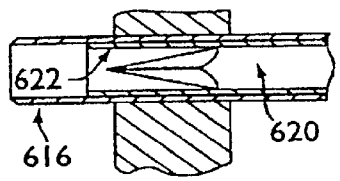
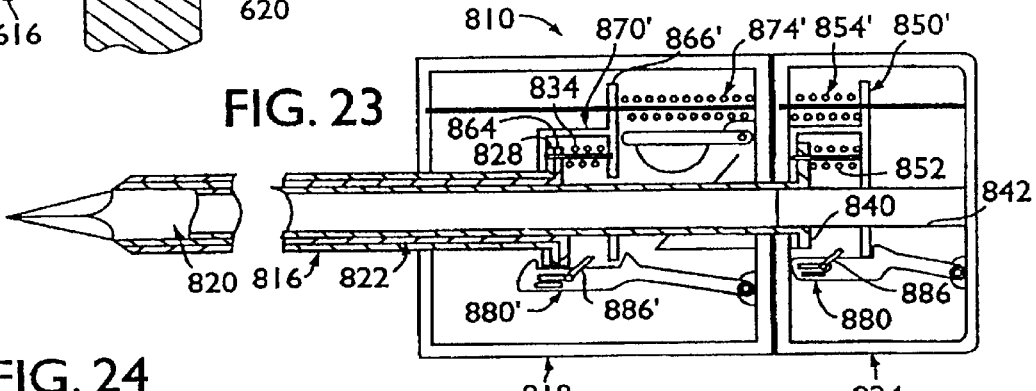
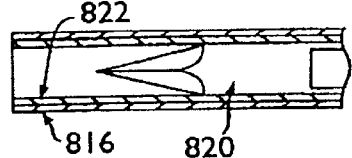

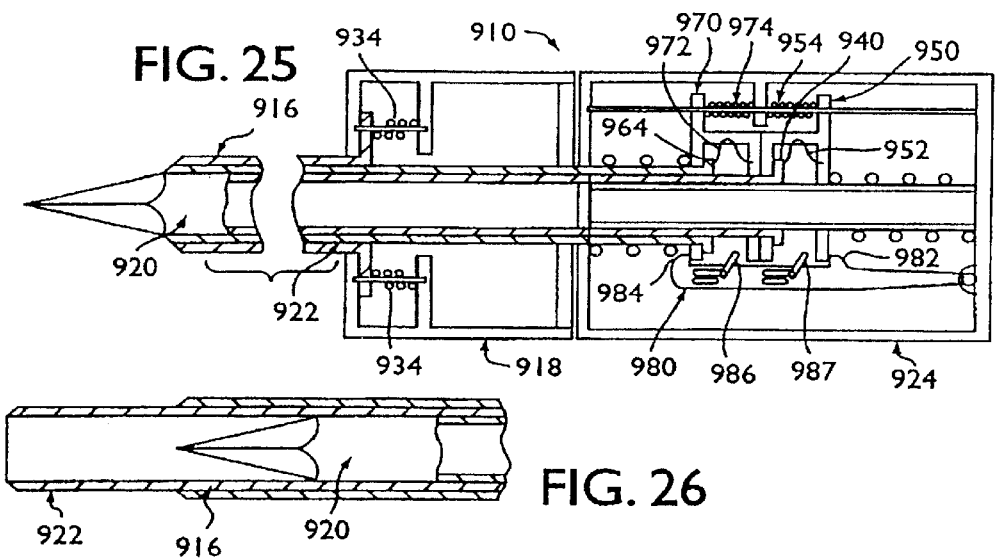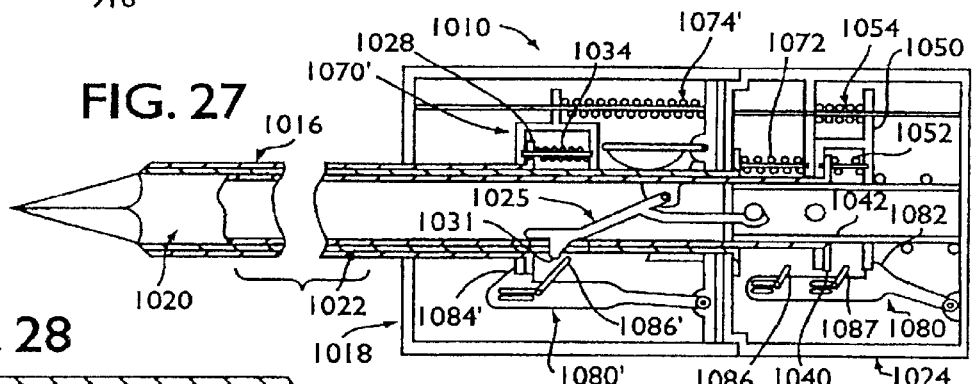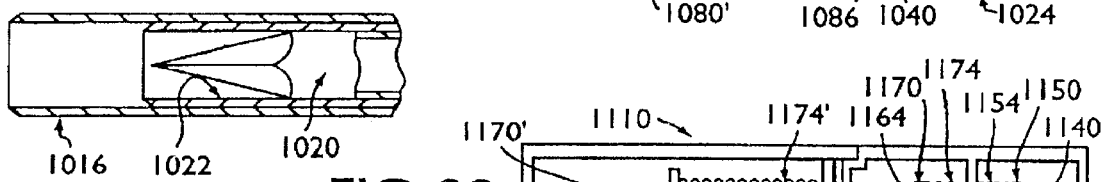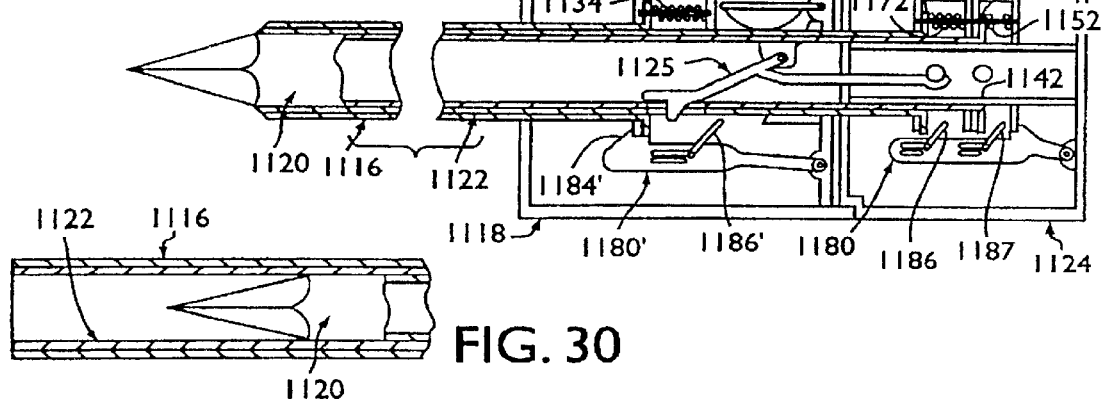

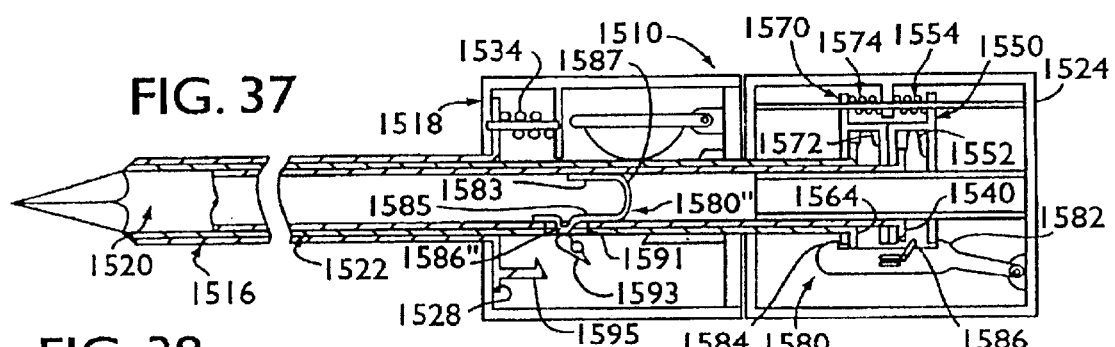
FIG. 37
FIG. 38
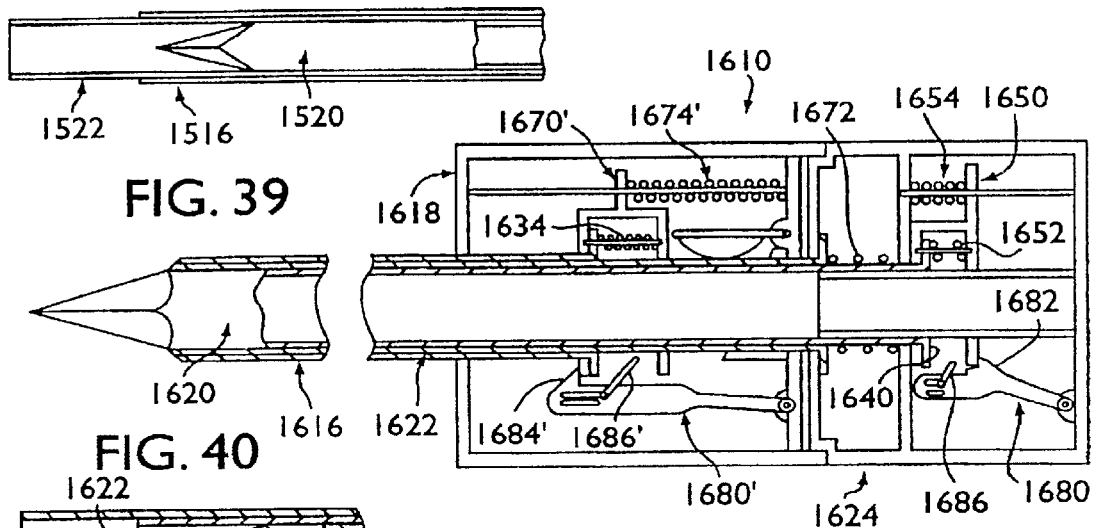
FIG. 39
FIG. 40
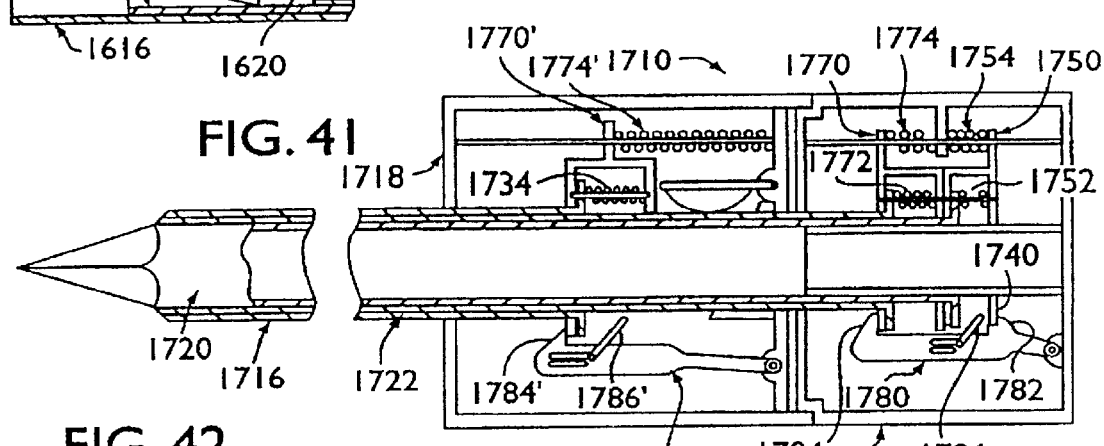
FIG. 41
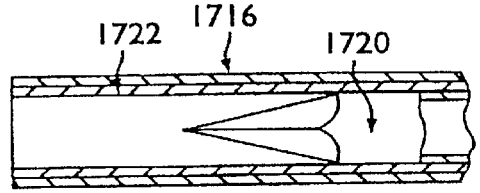
FIG. 42

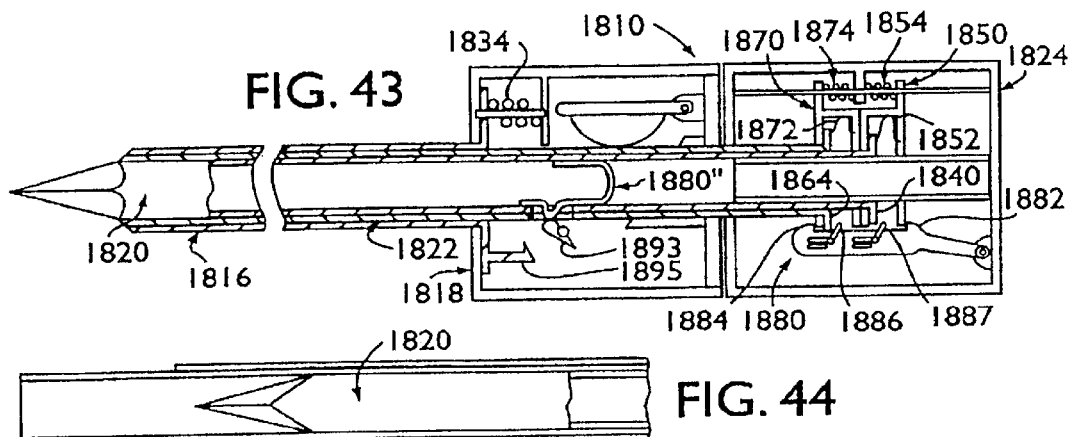
FIG. 43
FIG. 44
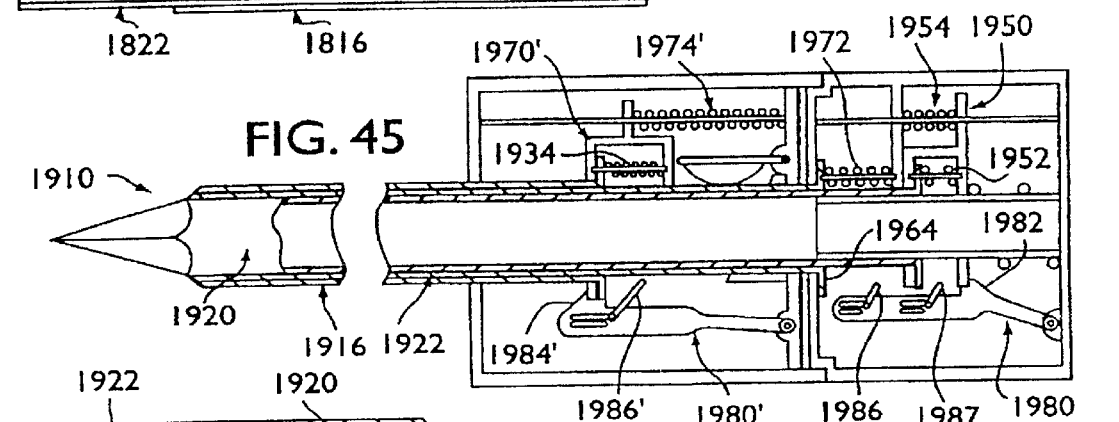
FIG. 45
FIG. 46
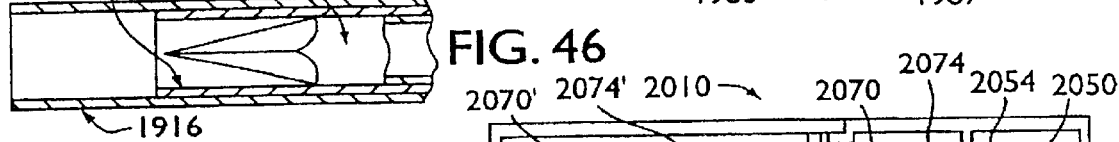
FIG. 47
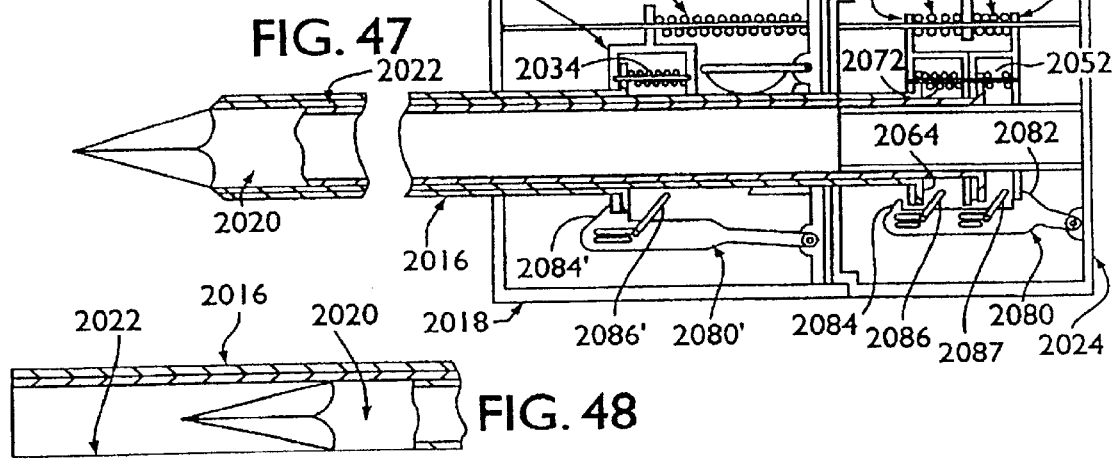
FIG. 48

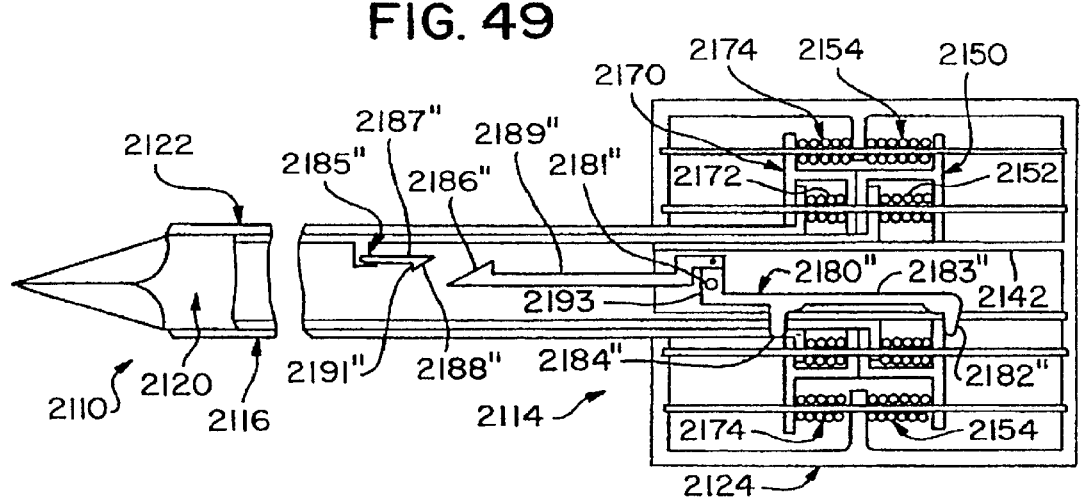
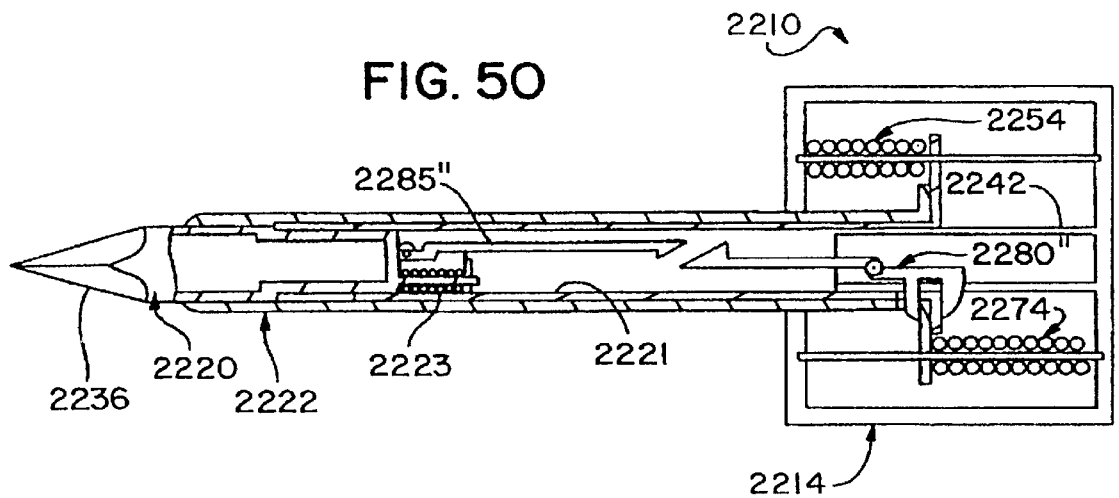

SAFETY PENETRATING INSTRUMENT WITH PROTECTIVE SHEATH, TRIGGERED PENETRATING MEMBER RETRACTION AND SINGLE AND SAFETY MEMBER PROTRUSION

CROSS-REFERENCE TO RELATED APPLICATIONS

This application is a division of application Ser. No. 08/279,170, now U.S. Pat. No. 5,645,556, filed Jul. 22, 1994 which is a continuation-in-part of applications Ser. No. 08/083,220, now U.S. Pat. No. 5,431,635, filed Jun. 24, 1993, which is a continuation-in-part of prior applications Ser. No. 07/628,899, now U.S. Pat. No. 5,226,426 filed Dec. 18, 1990 and Ser. No. 07/817,113, now U.S. Pat. No. 5,350,393, filed Jan. 6, 1992, Ser. No. 08/083,728, now U.S. Pat. No. 5,466,224, filed Jun. 29, 1993 which is a continuation-in-part of prior applications Ser. No. 07/628,899, now U.S. Pat. No. 5,226,426, filed Dec. 18, 1990 and Ser. No. 07/817,113, now U.S. Pat. No. 5,350,393, filed Jan. 6, 1992, Ser. No. 08/115,152, now U.S. Pat. No. 5,578,053, filed Sep. 2, 1993, and Ser. No. 08/177,616, still pending, filed Jan. 4, 1994, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to overcome the above-mentioned disadvantages of the prior art and to provide a safety penetrating instrument having a protected state wherein the penetrating member of the safety penetrating instrument is retracted and one or more safety members are extended to protrude distally beyond the penetrating member distal end.

It is another object of the present invention to trigger a safety penetrating instrument to move to a protected state, where the penetrating member of the safety penetrating instrument is retracted and one or more safety members of the safety penetrating instrument are extended to protrude distally beyond the penetrating member distal end in response to penetration of the safety penetrating instrument into an anatomical cavity.

Yet another object of the present invention is to utilize a safety shield or probe as a safety member in a safety penetrating instrument having a cannula, a penetrating member and a safety member and to trigger substantially simultaneous retraction of the penetrating member and protrusion of the safety member in response to penetration of the safety member into an anatomical cavity.

Still another object of the present invention is to utilize as a safety member the cannula of a safety penetrating instrument having a cannula, a penetrating member and a protective sheath and to trigger substantially simultaneous retraction of the penetrating member and protrusion of the cannula in response to penetration of the protective sheath into an anatomical cavity.

A further object of the present invention is to utilize the cannula and a safety shield or probe as safety members in a safety penetrating instrument having a cannula, a penetrating member and a safety shield or probe and to trigger substantially simultaneous retraction of the penetrating member and protrusion of both the cannula and the safety shield or probe in response to penetration of the safety shield or probe into an anatomical cavity.

Yet another object of the present invention is to utilize a safety shield or probe as a safety member in a safety penetrating instrument having a cannula, a penetrating member and a safety member and to trigger substantially simultaneous retraction of the penetrating member and protrusion of the safety member in response to penetration of the penetrating member into an anatomical cavity.

An additional object of the present invention is to utilize as a safety member the cannula of a safety penetrating instrument having a cannula, a penetrating member and a protective sheath and to trigger substantially simultaneous retraction of the penetrating member and protrusion of the cannula in response to penetration of the penetrating member into an anatomical cavity.

A still further object of the present invention is to utilize the cannula and a safety shield or probe as safety members in a safety penetrating instrument having a cannula, a penetrating member and a safety shield or probe and to trigger substantially simultaneous retraction of the penetrating member and protrusion of both the cannula and the safety shield or probe in response to penetration of the penetrating member into an anatomical cavity.

Still another object of the present invention is to utilize a safety shield or probe as a safety member in a safety penetrating instrument having a cannula, a penetrating member and a safety member and to trigger substantially simultaneous retraction of the penetrating member and protrusion of the safety member in response to penetration of the cannula into an anatomical cavity.

Still another object of the present invention is to utilize as a safety member the cannula of a safety penetrating instrument having a cannula, a penetrating member and a protective sheath and to trigger substantially simultaneous retraction of the penetrating member and protrusion of the cannula in response to penetration of the cannula into an anatomical cavity.

Yet a further object of the present invention is to utilize the cannula and a safety shield or probe as safety members in a safety penetrating instrument having a cannula, a penetrating member and a safety shield or probe and to trigger substantially simultaneous retraction of the penetrating member and protrusion of both the cannula and the safety shield or probe in response to penetration of the cannula into an anatomical cavity.

It is another object of the present invention to utilize a safety shield or probe as a safety member in a safety penetrating instrument having a cannula, a penetrating member and a safety member and to trigger substantially simultaneous retraction of the penetrating member and protrusion of the safety member in response to penetration of both the safety member and penetrating member into an anatomical cavity.

Another object of the present invention is to utilize as a safety member the cannula of a safety penetrating instrument having a cannula, a penetrating member and a protective sheath and to trigger substantially simultaneous retraction of the penetrating member and protrusion of the cannula in response to penetration of the protective sheath and penetrating member into an anatomical cavity.

A further object of the present invention is to utilize the cannula and a safety shield or probe as safety members in a safety penetrating instrument having a cannula, a penetrating member and a safety shield or probe and to trigger substantially simultaneous retraction of the penetrating member and protrusion of both the cannula and the safety shield or probe in response to penetration of the safety shield or probe and penetrating member into an anatomical cavity.

An additional object of the present invention is to utilize a safety shield or probe as a safety member in a safety penetrating instrument having a cannula, a penetrating member and a safety member and to trigger substantially simultaneous retraction of the penetrating member and protrusion of the safety member in response to penetration of the safety member and cannula into an anatomical cavity.

Still another object of the present invention is to utilize as a safety member the cannula of a safety penetrating instrument having a cannula, a penetrating member and a protective sheath and to trigger substantially simultaneous retraction of the penetrating member and protrusion of the cannula in response to penetration of the protective sheath and cannula into an anatomical cavity.

Yet a further object of the present invention is to utilize the cannula and a safety shield or probe as safety members in a safety penetrating instrument having a cannula, a penetrating member and a safety shield or probe and to trigger substantially simultaneous retraction of the penetrating member and protrusion of both the safety shield or probe and cannula in response to penetration of the safety shield or probe and cannula into an anatomical cavity.

It is another object of the present invention to utilize a safety shield or probe as a safety member in a safety penetrating instrument having a cannula, a penetrating member and a safety member and to trigger substantially simultaneous retraction of the penetrating member and protrusion of the safety member in response to penetration of the penetrating member and cannula into an anatomical cavity.

Another object of the present invention is to utilize as a safety member the cannula of a safety penetrating instrument having a cannula, a penetrating member and a protective sheath and to trigger substantially simultaneous retraction of the penetrating member and protrusion of the cannula in response to penetration of the penetrating member and cannula into an anatomical cavity.

A further object of the present invention is to utilize the cannula and a safety shield or probe as safety members in a safety penetrating instrument having a cannula, a penetrating member and a safety shield or probe and to trigger substantially simultaneous retraction of the penetrating member and protrusion of the cannula and the safety shield or probe in response to penetration of the penetrating member and cannula into an anatomical cavity.

Yet another object of the present invention is to utilize a safety shield or probe as a safety member in a safety penetrating instrument having a cannula, a penetrating member and a safety member and to trigger substantially simultaneous retraction of the penetrating member and protrusion of the safety member in response to penetration of the penetrating member, cannula, and the safety shield or probe into an anatomical cavity.

An additional object of the present invention is to utilize as a safety member the cannula of a safety penetrating instrument having a cannula, a penetrating member and a protective sheath and to trigger substantially simultaneous retraction of the penetrating member and protrusion of the cannula in response to penetration of the penetrating member, cannula and protective sheath into an anatomical cavity.

Still another object of the present invention is to utilize the cannula and a safety shield or probe as safety members in a safety penetrating instrument having a cannula, a penetrating member and a safety shield or probe and to trigger substantially simultaneous retraction of the penetrating member and protrusion of both the cannula and the safety shield or probe in response to penetration of the penetrating member, cannula and safety shield or probe into an anatomical cavity.

It is another object of the present invention to carry a probe on a safety penetrating instrument having a penetrating member, cannula and safety member, and to trigger substantially simultaneous retraction of the penetrating member and protrusion of one or both of the cannula and safety member in response to proximal movement of the probe a predetermined proximal distance.

It is an additional object of the present invention to mount the penetrating member, cannula and safety member of a safety penetrating instrument with a continuous distal bias and to align chamfered ends of the retracted cannula and safety member with a proximal end of a tapered distal portion of the extended penetrating member to ease penetration.

An additional object of the present invention is to provide a safety penetrating instrument having an operating member movable proximally during penetration of an anatomical cavity wall and distally upon introduction of the safety penetrating instrument into the anatomical cavity to trigger release of one or more safety members to move distally to an extended protruding position and release of a penetrating member to move proximally to a retracted position.

The present invention has as an additional object to increase the force biasing one or more safety members distally in a safety penetrating instrument to assure protrusion of the safety members upon penetration of the safety penetrating instrument into an anatomical cavity while minimizing the force-to-penetrate required.

A still further object of the present invention is to provide a safety penetrating instrument having independent trigger mechanisms for triggering retraction of a penetrating member and protrusion of one or more safety members upon penetration of the safety penetrating instrument into an anatomical cavity.

Some of the advantages of the present invention over the prior art are that either or both of the cannula and a separate safety member, such as a shield or probe, can serve to protect the distal end of the penetrating member within an anatomical cavity, that the distal bias force on the safety member and/or cannula can be designed to assure protrusion of the safety member and/or cannula regardless of the anatomical tissue being penetrated, that penetration of an anatomical cavity wall by the safety penetrating instrument can be commenced with the safety member and/or cannula in a retracted position exposing the sharp tip of the penetrating member, that the distal bias to move the safety member and/or cannula into an extended position is not required to be overcome during penetration of the anatomical cavity wall, that retraction of the penetrating member and protrusion of the safety member and/or cannula can be achieved with a single latch and trigger mechanism, with separate independent latch and trigger mechanisms, with a single latch and multiple triggers, or with multiple latches and single or multiple triggers to achieve varying degrees of redundant safety, that the safety and efficacy of the safety penetrating instrument can be enhanced, that at least two modes of safety are provided for redundantly protecting the tip of the penetrating member within an anatomical cavity with at least one mode of safety persisting to protect the tip upon withdrawal of the penetrating member from the anatomical cavity, that in some instances the overall length of the safety penetrating instrument can be reduced, and that the retractable safety penetrating instrument of the present invention can be inexpensively manufactured with minimum components to reduce cost, facilitate sterilization for reuse and allow economical, single-patient use.

The present invention is generally characterized in a safety penetrating instrument having a cannula, a penetrating member disposed within the cannula, and a safety member, such as a shield or probe, movable relative to the penetrating member between a retracted position exposing the distal end of the penetrating member and an extended position covering the distal end of the penetrating member. The penetrating member is movable in a proximal direction from an extended position toward a retracted position with retracting means and at least one of the cannula and safety member is movable distally from a retracted position toward an extended position with extending means. Locking means, such as one or more spring-biased latches, lock the penetrating member in the extended position and at least one of the cannula and safety member in the retracted position and are released with releasing means, such as trigger levers, responsive to entry of the safety penetrating instrument into the anatomical cavity. One or more of the proximal ends of the penetrating member, safety member and cannula can be mounted by collars or rail members and biased to move distally within the collars or rail members thereby permitting substantially uniform proximal movement of the members during penetration of the anatomical cavity wall to ease insertion and causing distal movement upon penetration into the anatomical cavity to trigger release of the locking means.

Another aspect of the present invention is generally characterized in a method of forming a portal in a wall of an anatomical cavity including the steps of penetrating the anatomical cavity wall with a penetrating member of a safety penetrating instrument having a protective state where the penetrating member is moved proximally toward a retracted position and at least one of a cannula and a safety member of the safety penetrating instrument is moved distally toward an extended position to protect a distal end of the penetrating member. The safety penetrating instrument is triggered to move to the protective state when the safety penetrating instrument enters the anatomical cavity.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

BRIEF DESCRIPTION OF THE DRAWINGS

FIG. 1 is a broken side view, partly in section, of a safety penetrating instrument according to the present invention.

FIG. 2 is a broken perspective view, partly in section, of the extending collar of the safety penetrating instrument of FIG. 1.

FIG. 3 is a broken perspective view, partly in section, of the retracting collar of the safety penetrating instrument of FIG. 1.

FIGS. 4–7 are broken views, partly in section, illustrating use of the safety penetrating instrument of the present invention.

FIG. 8 is a broken side view, partly in section, of another safety penetrating instrument according to the present invention.

FIG. 9 is a broken perspective view, showing the protrusion formed on a safety member of the safety penetrating instrument of FIG. 8.

FIG. 10 is a view of the distal portion of the safety penetrating instrument of FIG. 8 with the tip of the penetrating member in the protected state.

FIG. 11 is a broken side view, partly in section, of another modified safety penetrating instrument according to the present invention.

FIG. 12 is a side view, partly in section, of the distal end of the safety penetrating instrument of FIG. 11 with the tip of the penetrating member in the protected state.

FIG. 13 is a broken side view, partly in section, illustrating a further modified safety penetrating instrument according to the present invention.

FIG. 14 is a side view, partly in section, of the distal end of the safety penetrating instrument of FIG. 13 with the tip of the penetrating member in the protected state.

FIG. 15 is a broken side view, partly in section of yet another modified safety penetrating instrument according to the present invention.

FIG. 16 is a side view, partly in section, of the distal end of the safety penetrating instrument of FIG. 15 with the tip of the penetrating member in the protected state.

FIG. 17 is a broken side view, partly in section, of an additional modified safety penetrating instrument according to the present invention.

FIG. 18 is a side view, partly in section, of a distal end of the safety penetrating instrument of FIG. 17.

FIG. 19 is a broken side view, partly in section, of still another safety penetrating instrument according to the present invention.

FIG. 20 is a side view, partly in section, of the distal end of the safety penetrating instrument of FIG. 19.

FIG. 21 is a broken side view, partly in section, of yet a further safety penetrating instrument according to the present invention.

FIG. 22 is a side view, partly in section, of the distal end of the safety penetrating instrument of FIG. 21.

FIG. 23 is another safety penetrating instrument according to the present invention.

FIG. 24 is a side view, partly in section, showing the distal end of the safety penetrating instrument of FIG. 23 with the tip of the penetrating member in a retracted, protected state.

FIG. 25 is a broken side view, partly in section, of a further safety penetrating instrument according to the present invention.

FIG. 26 is a side view, partly in section, of the distal end of the safety penetrating instrument of FIG. 25 with the tip of the penetrating member in a retracted, protected state.

FIG. 27 is a broken side view, partly in section, of a safety penetrating instrument according to the present invention.

FIG. 28 is a side view, partly in section, of the distal end of the safety penetrating instrument of FIG. 27, showing the tip of the penetrating member in a retracted protected state.

FIG. 29 is yet another safety penetrating instrument according to the present invention.

FIG. 30 is a side view, partly in section, of the distal end of the safety penetrating instrument of FIG. 29, showing the tip of the penetrating member in a retracted, protected state.

FIG. 37 is a broken side view, partly in section, of a further safety penetrating instrument according to the present invention.

FIG. 38 is a side view, partly in section, of the distal end of the safety penetrating instrument of FIG. 37 showing the tip of the penetrating member in a retracted, protected state.

FIG. 39 is a broken side view, partly in section, of yet another safety penetrating instrument according to the present invention.

FIG. 40 is a side view, partly in section, of the distal end of the safety penetrating instrument of FIG. 39 with the tip of the penetrating member in a retracted, protected state.

FIG. 41 is a broken side view, partly in section, of an additional safety penetrating instrument according to the present invention.

FIG. 42 is a side view, partly in section, of the distal end of the safety penetrating instrument of FIG. 41 with the tip of the penetrating member in a retracted, protected state.

FIG. 43 is a broken side view, partly in section, of still another safety penetrating instrument according to the present invention.

FIG. 44 is a side view, partly in section, of the distal end of the safety penetrating instrument of FIG. 43 showing the tip of the penetrating member in a retracted, protected state.

FIG. 45 is a broken side view, partly in section, of yet a further safety penetrating instrument according to the present invention.

FIG. 46 is a side view, partly in section, showing the distal end of the safety penetrating instrument of FIG. 45 with the tip of the penetrating member in a retracted, protected state.

FIG. 47 is a broken side view, partly in section, of yet still another safety penetrating instrument according to the present invention.

FIG. 48 is a side view, partly in section, showing the distal end of the safety penetrating instrument of FIG. 47 with the tip of the penetrating member in a protected state.

FIG. 49 is a broken side view, partly in section, of a penetrating unit for use with the safety penetrating instrument of the present invention.

FIG. 50 is a broken side view, partly in section, of another penetrating unit for use with the safety penetrating instrument of the present invention.

DESCRIPTION OF THE PREFERRED EMBODIMENTS

Figure 4:
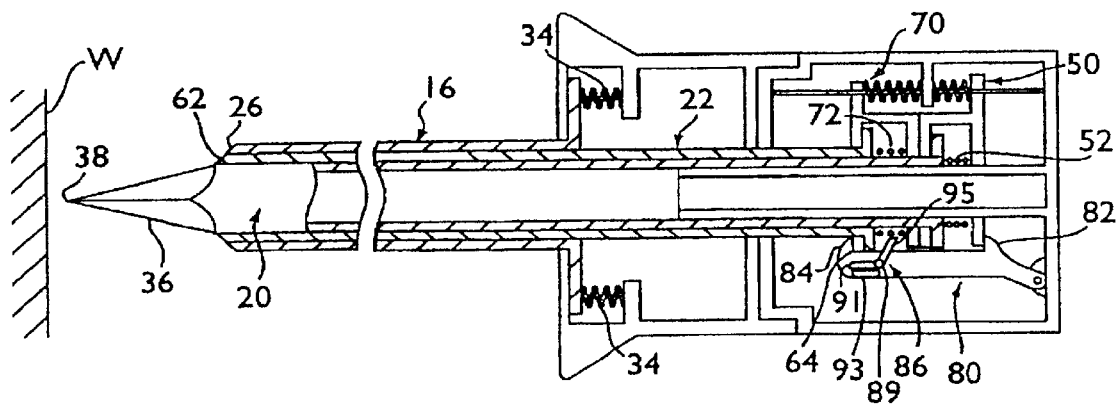

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

A safety penetrating instrument 10 according to the present invention, as shown in FIG. 1, is formed of a portal unit 12 and a penetrating unit 14. The portal unit 12 includes a cannula in the form of an elongate portal sleeve 16 and a housing 18 mounting a proximal end of the portal sleeve 16. The penetrating unit 14 includes an elongate penetrating member 20, shown as a trocar, disposed in the portal sleeve 16, a safety member in the form of an elongate tubular safety shield 22 and a hub 24 mounting proximal ends of the penetrating member 20 and the safety shield 22. The hub 24 can be latched to the housing 18 with the use of any suitable releasable mechanism, such as detents operated by buttons, allowing the hub to be removed from the housing withdrawing the penetrating member and the safety shield from the portal sleeve.

The portal unit 12 can be made of any desirable, medical grade materials depending on procedural use and desirability of being for single patient use or reusable. The portal sleeve 16 is tubular and can be cylindrical as shown or have any other desired configuration in cross-section in accordance with the procedure to be performed and the anatomical cavity to be penetrated. Portal sleeve 16 is preferably made of a substantially cylindrical length of rigid or flexible, transparent or opaque material, such as stainless steel or other medically acceptable plastic or metal material, and defines a lumen for receiving penetrating member 20. Portal sleeve 16 terminates distally at a distal end 26, which can be faced-off, have rounded edges or be chamfered as shown, and proximally in a transverse tab or flange 28 disposed within the housing 18 between a front wall 30 of the housing and a pair of opposed transverse ribs 32 proximally spaced from the front wall 30 and secured to the housing. Springs 34 are held in compression between the transverse flange 28 and the ribs 32 to bias the portal sleeve flange 28 distally into abutment with the front wall 30 while permitting proximal movement of the flange 28 toward the ribs 32.

The housing 18 can be made of any desirable material, such as plastic or metal, and can have any desirable configuration to facilitate grasping by a surgeon and is preferably constructed to sealingly engage instruments passing therethrough and to include a valve biased to a closed state when no instrument passes through the portal sleeve.

Penetrating member 20 includes a shaft or body terminating distally at a distal end 36 having a tip or point 38 for penetrating anatomical tissue and proximally at a transverse flange 40 disposed in hub 24 with the body of the penetrating member passing through an opening in a front wall 41 of the hub longitudinally aligned with the portal sleeve 16. The penetrating member distal end 36 can have any configuration desired for a particular procedure, for example, the pyramidal trocar configuration shown or conical, threaded, multifaceted, blunt, open, slanted or needle configurations. The penetrating member 20 can be made of any suitable, medical grade materials and can be made of multiple components such that, for example, the distal end 36 can be made of stainless steel and secured in any conventional manner, such as by threads, to the shaft or body which can be tubular and made of a less expensive material, such as plastic or metal. The body of the penetrating member 20 is hollow or tubular or partly hollow or tubular to receive a guide tube 42 extending distally from a rear wall 44 of the hub 24.

A rail member or retracting collar 50 is disposed in housing 18 and is generally U-shaped in configuration including a proximal wall 46 disposed transverse or perpendicular to a longitudinal axis of the safety penetrating instrument 10, a distal wall 48 parallel to proximal wall 46 and a side wall 47 transversely joining the retracting collar proximal and distal walls 46 and 48. Side wall 47 is also shown carrying a raised projection or ridge 49 which extends perpendicularly from side wall 47 and is oppositely disposed of the retracting collar proximal and distal walls 46 and 48. As best seen in FIG. 2, the transverse flange 40 of the penetrating member 20 is captured between the walls 46 and 48 of retracting collar 50, with retracting collar proximal wall 46 defining an opening configured to allow passage therethrough by the guide tube 42 and retracting collar distal wall 48 defining an opening to allow passage therethrough by the shaft or body of penetrating member 20. A bias member 52 is connected between the transverse flange 40 of the penetrating member and the proximal wall 46 of the retracting collar 50 to bias the penetrating member in a distal direction such that flange 40 is biased in abutment with the retracting collar distal wall 48. Bias member 52 is shown as a helical coil spring disposed around the guide tube 42 and held in compression between the flange 40 and retracting collar proximal wall 46; however, bias member 52 can include any other type of spring or other bias device including tension springs, compression springs, torsion springs, pan springs, rubber, plastic or magnets, for example.

A retracting member 54 is connected between the collar 50 and a transverse internal wall 56 of the hub 24 to bias the collar 50 and thus the penetrating member 20 in a proximal direction to the retracted position shown in FIG. 1 where the tip 38 of the penetrating member is disposed within the safety shield 22. As shown, retracting member 54 is formed of a helical coil spring 58 mounted around a guide rod 60 in compression between the internal wall 56 and the retracting collar ridge 49; however, the retracting member can include various other types of springs or other bias devices such as tension springs, torsion springs, leaf springs, rubber, plastic or magnets, for example, and one or more than one retracting member can be provided.

Safety shield 22 is disposed between penetrating member 20 and portal sleeve 16 and can be cylindrical or have any other desired configuration in cross-section in accordance with the respective shapes of the penetrating member 20 and the portal sleeve 16 to be telescopically fitted therebetween. Safety shield 22 is preferably made of a substantially cylindrical length of rigid or flexible, transparent or opaque material, such as stainless steel or other medically acceptable plastic or metal material, and can be open as shown or form a cover at a distal end to protect the tip 38 of the penetrating member 20. Safety shield 22 terminates distally in a distal end 62, which can be faced-off, have rounded edges or be chamfered as shown, and terminates proximally in a transverse flange 64 mounted within the hub 24.

An extending collar 70, similar to retracting collar 50, is disposed within the hub 24 and has a generally U-shaped configuration with spaced, parallel proximal and distal walls 66 and 68, and a side wall 67 connecting the extending collar proximal and distal walls 66 and 68. A protrusion or ridge 69 extends perpendicularly from the side wall 67 opposite the proximal and distal walls 66 and 68. As best seen in FIG. 3, the proximal wall 66 of the extending collar 70 defines an opening for allowing passage of the penetrating member 20 therethrough, and the safety shield 22 passes through aligned openings in the front wall 41 of the hub 24 and the extending collar distal wall 68, with the transverse tab or flange 64 being disposed between the extending collar proximal and distal walls 66 and 68. A bias member 72 is connected between the transverse flange 64 of the safety shield 22 and the proximal wall 66 of the extending collar 70 to bias the safety shield 22 distally toward the distal wall 68 of the extending collar 70. Bias member 72, like bias member 52, is shown as a helical coil spring disposed around a guide shaft; however, bias member 72 can include any other type of spring or bias device as previously discussed. An extending member 74 is mounted between the extending collar ridge 69 and the transverse internal wall 56 to bias the safety shield 22 in a distal direction to the protruding position shown in FIG. 1 where the distal end 62 of the safety shield 22 protrudes beyond the tip 38 of the penetrating member 20. As shown, extending member 74 is formed of a helical coil spring 76 surrounding a guide rod 78 and is mounted in compression between the transverse internal wall 56 and extending collar ridge 69; however, the extending member can include various other types of spring or other biased devices such as tension springs, torsion springs, leaf springs, rubber, plastic or magnets, for example, and one or more than one extending member can be provided.

A latch 80 extends distally from the rear wall 44 of the hub 24 to lock the retracting and extending collars 50 and 70 as shown in FIG. 4. The latch 80 includes an upwardly angled arm 83 rotatably mounted on a pivot 81 secured to the rear wall 44 of the hub 24 and a distal extension 85 joining the arm 83 at a bend 87. A torsion spring (not shown) is coiled around the pivot 81 and fixed to the latch 80 to bias the latch clockwise looking at FIG. 4. Other bias devices such as a tension spring or leaf spring held in compression between a side wall of the hub and the latch, or rubber, plastic or magnetic elements, can also be used to bias the latch. A first latching protrusion or pawl 82 is formed at the proximal end of distal extension 85 for engaging the retracting collar 50 and includes a curved proximal edge configured to allow distal movement of transverse flange 40 of the penetrating member over the pawl 82, and a straight transverse distal edge to restrict proximal movement of the flange 40 past the pawl 82. A second latching protrusion or pawl 84 is formed at the distal end of distal extension 85 for engaging the extending collar 70 and includes a distal edge configured to allow proximal movement of transverse flange 64 of safety shield 22 over the pawl 84 and a proximal edge configured to prohibit distal movement of the flange 64 past the pawl 84. As shown in FIG. 4, pawls 82 and 84 are spaced to allow both collars 50 and 70 to be held therebetween; however, the pawls can be spaced closer or further apart to engage any other feature of the collars or structures carried by the collars. A trigger lever 86 is rotatably mounted on a pin 89 disposed intermediate the proximal and distal pawls 82 and 84 and is generally L-shaped, including a leg 91 extending parallel the distal extension 85 above a nub 93 and a leg 95 extending transversely and at a slight angle to be positioned proximally of the safety member flange 64 when the safety member 22 is retracted and the flange 64 is biased against extending collar distal wall 68. A torsion spring (not shown), or the like, is connected between the pin 89 and the trigger lever 86 to bias the trigger lever 86 counterclockwise looking at FIG. 4 so that leg 91 normally abuts nub 93. Handles 88 and 90, shown in phantom in FIG. 1, are connected with the proximal ends of the penetrating member 20 and the safety shield 22, respectively, and are movable towards one another along a single continuous slot 92 or a pair of collinear slots for use in moving the penetrating member 20 from the retracted position of FIG. 1 to the extended position, shown in FIG. 4, and the safety shield 22 from the extended position of FIG. 1 to the retracted position, shown in FIG. 4, whereby the tip 38 of the penetrating member 20 is disposed distally of the portal sleeve distal end 26 and the safety shield distal end 62. The handles can be operated together or separately to selectively extend the penetrating member and/or retract the safety shield as desired.

In use, the safety penetrating instrument 10 will normally be provided in the condition illustrated in FIG. 1 with the safety shield 22 in the extended position and the penetrating member 20 in the retracted position where the tip 38 of the penetrating member is disposed proximally of the distal end 62 of the safety shield 22 in a safe, unexposed and protected position. With the penetrating member 20 in the retracted position, retraction collar 50 will be biased in abutment with the rear wall 44 of hub 24, and handle 88 will be disposed at a proximal end of the slot 92. Conversely, extending collar 70 will be biased in abutment with the front wall 41 of the hub 24, and handle 90 will be disposed at the distal end of the slot 92. With the safety penetrating instrument 10 provided in the condition illustrated in FIG. 1, the latch 80 will be disposed intermediate the distal wall 48 of retracting collar 50 and the proximal wall 66 of extending collar 70. Prior to commencing penetration of an anatomical cavity wall, handles 88 and 90 are grasped individually or together and manually moved within slot 92 towards one another camming the latch 80 away from the penetrating member 20 to allow walls 48 and 66 of collars 50 and 70, respectively, to pass over the proximal and distal pawls 82 and 84. Latch 80 will spring back towards the collars; however, continued movement of handles 88 and 90 toward one another within slot 92 causes trailing walls 46 and 68 to cam the latch 80 away from penetrating member 20 once again to allow these walls to pass over proximal and distal pawls 82 and 84 as well. Once all walls of the collars 50 and 70 are disposed intermediate the proximal and distal pawls 82 and 84 of the latch 80, the latch 80 will spring inward to lock the collars, and thus the penetrating member 20 and safety shield 22, in the condition shown in FIG. 4 wherein the penetrating member 20 is locked in the extended position and the safety shield 22 is locked in the retracted position.

Figure 5:
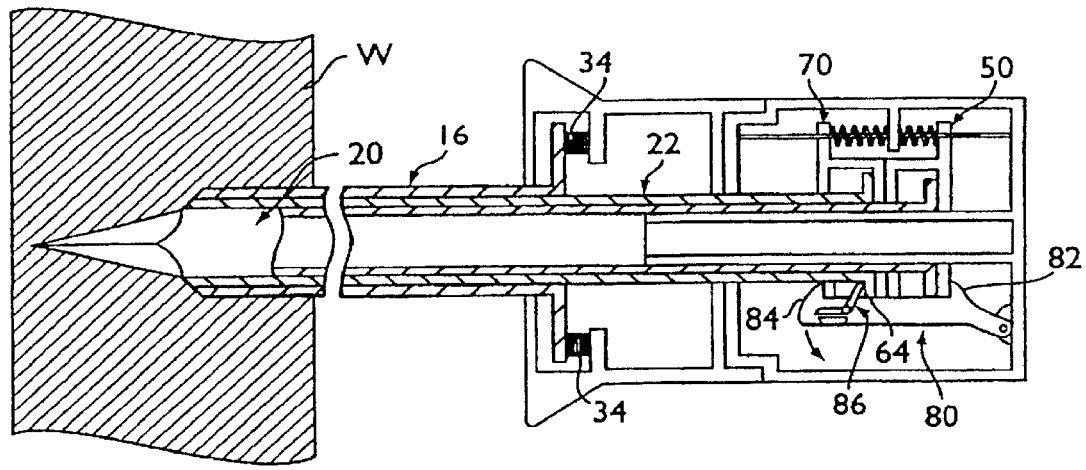
Figure 6:
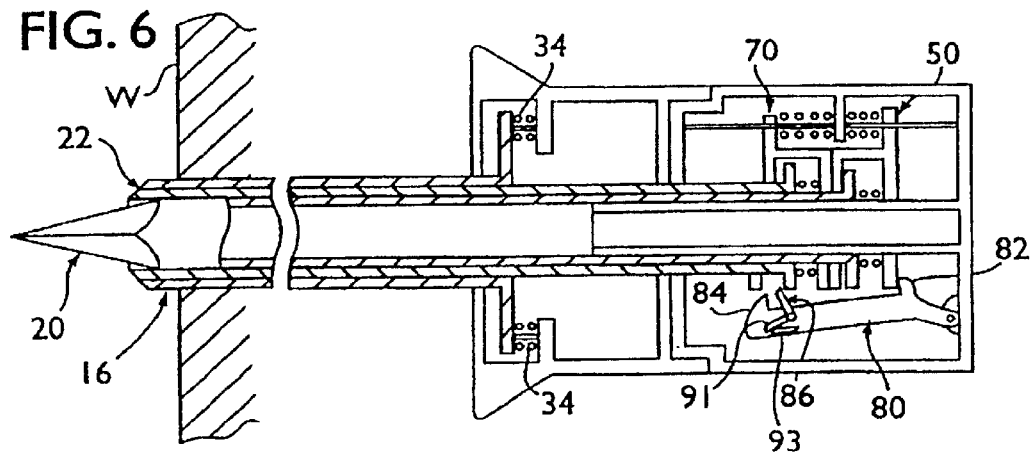

The safety penetrating instrument 10 is now ready to be utilized to penetrate an anatomical cavity wall W. During penetration of the anatomical cavity wall W, the portal sleeve 16, penetrating member 20 and safety shield 22 are moved together through the tissue, the retracting and extending collars 50 and 70 remaining locked between pawls of the latch 80. The portal sleeve 16 is moved proximally relative to housing 18 against the distal bias of springs 34 due to contact of the portal sleeve 16 with the anatomical cavity wall W as shown in FIG. 5. Similarly, the proximal ends of the penetrating member 20 and safety shield 22 are moved proximally within collars 50 and 70 against the distal bias of springs 52 and 72, respectively, due to contact of these members with the anatomical cavity wall W. Movement of the safety shield 22 proximally causes proximal movement of flange 64 over leg 95 of trigger lever 86 causing the lever 86 to rotate in a clockwise direction looking at FIG. 5 and subsequently to spring back to a transverse position after the flange 64 has advanced beyond the trigger leg 95. Retracting and extending collars 50 and 70 will remain in the locked condition between proximal and distal pawls 82 and 84 until safety shield 22 penetrates through anatomical cavity wall W to emerge on the other side thereof into the anatomical cavity as shown in FIG. 6. Because there is no anatomical tissue ahead of the safety shield 22 to contact the distal end 62 of the safety shield 22, the safety shield 22 moves distally under the distal bias of spring 72 to bear distally against leg 95 of trigger lever 86. The trigger lever 86 is thus rotated counterclockwise until leg 91 bears against nub 93 and is stopped. The distal force exerted against the lever 86 creates a moment which rotates latch 80 away from the extending and retracting collars 70 and 50 to allow retraction of the penetrating member 20 under the influence of retracting member 54 and to permit extension of the safety shield 22 under the influence of extending member 74. As shown in FIG. 7, when the penetrating member 20 is in the retracted position and the safety shield 22 is in the extended position, the tip 38 of the penetrating member is disposed proximally of the distal end 62 of the safety shield 22 in an unexposed, protected state. The hub 24 can then be safely withdrawn from the housing 18 allowing the portal sleeve 16 to remain in place for conducting various procedures via the lumen of the portal sleeve 16.

In the safety penetrating instrument 10, the safety shield 22 serves as both an operating member to trigger movement of the safety penetrating instrument to the protected state and as a safety member triggered to protrude into an anatomical cavity. By providing a safety penetrating instrument having a safety shield biased to move distally upon penetration into an anatomical cavity to trigger simultaneous release of the safety shield to move further distally under the influence of an extending member to a fully extended position and release of the penetrating member to move proximally under the influence of a retracting member to a retracted position, the distal force exerted by the extending member can be increased while minimizing the force required to penetrate the anatomical cavity wall. Since the safety shield is locked in the retracted position against the distal force exerted by the extending member during penetration, it is possible to select the distal force so as to assure protrusion of the safety shield regardless of the anatomical tissue being penetrated while not requiring that the distal force be overcome during penetration of the anatomical cavity wall. Additionally, since the penetrating member 20, safety shield 22 and portal sleeve 16 are all mounted on springs allowing a predetermined amount of proximal movement thereof, the portal sleeve and safety shield distal ends 26 and 62 can be chamfered and aligned with the tapered portion of the penetrating member distal end 36 to create, in the extended state shown in FIG. 4, a smooth profile that is maintained during penetration of the anatomical cavity wall by allowing the members to move together proximally during penetration as shown in FIG. 5.

The components of the safety penetrating instrument of the present invention can be made of any suitable, medical grade materials to permit sterilization for reuse or for single patient use. The components can be made of multiple parts or various configurations and materials to reduce cost. The portal unit can have various valves, stop cocks and seals in the housing to control fluid flow of air through and various adapters to adjust to the size of the instruments inserted through the portal unit. Additionally, the latch carrying the trigger lever can be part of the portal unit or the penetrating unit allowing the triggering mechanism to remain in place with the portal unit or to be withdrawn with the penetrating unit.

With the safety penetrating instrument of the present invention, retraction of the penetrating member and extension of the safety shield can be confirmed by movement of handles 88 and 90 along slot 92 and can be felt by the surgeon to provide both visual and tactile confirmation of penetration.

The locking and releasing mechanism requires only a latch for locking the penetrating member in the extended position and the safety shield in the retracted position and a trigger member for releasing the latch subsequent to proximal movement of the safety member followed by distal movement thereof upon penetrating into an anatomical cavity. It will be appreciated that various mechanisms can be employed to produce the locking and releasing functions of the present invention, such as, for example, multiple movably or pivotally mounted cams or pawls. It will also be appreciated that the locking and releasing mechanism can be positioned within the safety penetrating instrument in many various ways to minimize the length of the housing and/or the hub and, therefore, the overall length of the safety penetrating instrument.

A modification of the safety penetrating instrument 10 is shown in FIG. 8 with the primary difference being that penetration of a protective sheath into the anatomical cavity triggers automatic retraction of the penetrating member and simultaneous protrusion of the portal sleeve. Like safety penetrating instrument 10, the modified safety penetrating instrument 110 includes a portal unit 112 having a housing 118 mounting the proximal end of a portal sleeve 116, and a penetrating unit 114 having a hub 124 mounting the proximal end of a penetrating member 120. However, instead of a safety shield triggered to protrude as a safety member, the modified safety penetrating instrument 110 utilizes the portal sleeve 116 as a safety member and includes, as an operating member, a protective sheath 122 into which the penetrating member 120 retracts for safe withdrawal of the penetrating unit 114 from the portal unit 112. The protective sheath 122 is not triggered to protrude as a safety member, but is distally biased to normally protrude beyond the tip of the penetrating member upon withdrawal of the penetrating unit to prevent inadvertent contact with the tip.

Portal sleeve 116 terminates proximally in a transverse tab or flange 128 disposed between spaced transverse walls 166' and 168' of an extending collar 170' that is similar to collar 70, but mounted within the housing 118 rather than the hub 124. The proximal wall 166' of the extending collar 170' defines an opening configured to allow passage of the protective sheath 122 therethrough and is connected to the distal wall 168' by a side wall 167'. The distal wall 168' defines an opening configured to allow passage of the portal sleeve 116 therethrough. An extending member 174' in the form of a helical spring 176' surrounding a guide rod 178' is held in compression between a rear wall 177 of the housing 118 and the extending collar 170'. It will be appreciated, however, that the extending member 174' can include various other types of springs or other bias devices as previously described. A spring 134, similar to spring 34, is held in compression between the transverse flange 128 of the portal sleeve 116 and the proximal wall 166' of the extending collar 170' to bias the portal sleeve distally toward the distal wall 168' of the collar 170', while permitting a predetermined amount of proximal movement thereof.

A first latch 180', similar to latch 80, is mounted within the housing 118 to extend distally from the rear wall 177 of the housing 118 and to be biased toward the portal sleeve 116. Latch 180' includes a pawl 184' formed at a distal end and configured to engage the distal wall 168' of the extending collar 170' so as to permit proximal movement of the collar over the pawl while preventing distal movement when engaged. Latch 180' also carries a trigger lever 186' proximally spaced from pawl 184' and transversely extending toward the protective sheath 122. The trigger lever 186' is rotatable clockwise looking at FIG. 8, and is biased to return to its original transverse position.

Protective sheath 122 is generally tubular and can be formed of any suitable material to have a hollow configuration conforming to the configuration of the penetrating member 120. The sheath 122 includes a tab or protrusion 152 formed intermediate the protective sheath proximal and distal ends so as to be distally located relative to the trigger lever 186' when the safety penetrating instrument 110 is in the extended state shown in FIG. 8. As best seen in FIG. 9, the protrusion 152 is formed from a tongue of material cut from the tubular protective sheath 122 and configured to present a distally facing abutment surface 156 for engaging the trigger lever 186'. The protective sheath 122 terminates distally in a transverse flange 164 disposed between the front wall 141 of the hub 124 and a transverse wall 132 spaced proximally from the front wall 141 and secured to the hub 124, and is distally biased by a spring 172 held in compression between the flange 164 and the transverse wall 132. The wall 132 defines an opening for passage of penetrating member 120, which is essentially the same as penetrating member 20, but which terminates proximally in a longer transverse flange 140 disposed proximally of the transverse wall 132. A retracting member 154 in the form of a helical spring 158 surrounding a guide rod 160 is held in compression between the front wall 141 of the hub 124 and the transverse flange 140 to proximally bias the penetrating member 120 toward the retracted position shown in FIG. 10.

A second latch 180, similar to latch 80, extends distally from the rear wall 144 of the hub 124 to engage the transverse flange 140 of the penetrating member 120 to prevent proximal movement thereof when locked. The latch 180 includes a pawl 182 formed intermediate the latch proximal and distal ends for engaging the transverse flange 140 to prevent proximal movement thereof while permitting distal movement from the retracted position to the extended position shown in FIG. 8. A trigger lever 186 is rotatably carried near the distal end of the latch 180 and extends transversely toward the penetrating member 120 to be positioned proximally of the transverse flange 164 of the protective sheath 122 when the sheath 122 is biased against the front wall of the hub 124.

In operation, the safety penetrating instrument 110 is provided as shown in FIG. 10 with the portal sleeve distal end 126 extending distally beyond the protective sheath distal end 162, and the tip 138 of the penetrating member 120 spaced proximally of the protective sheath distal end 162. Handles, such as handles 88 and 90 previously described, are used to extend the penetrating member 120 and retract the portal sleeve 116 to the positions shown in FIG. 8 where they are locked in place by latches 180 and 180', respectively. Portal sleeve 116 and protective sheath 122 move together proximally during penetration of an anatomical cavity wall against the distal bias of springs 172 and 134 to maintain the alignment of their distal ends; however, it is distal movement of the protective sheath 122 upon penetrating into the anatomical cavity that ultimately triggers retraction of the penetrating member 120 and extension of the portal sleeve 116. More specifically, during penetration into the cavity wall, the protrusion 152 formed in protective sheath 122 bears against trigger lever 186' while the transverse flange 164 of the protective sheath 122 bears against trigger lever 186, causing both trigger levers to rotate clockwise looking at FIG. 8 to allow passage of the protrusion 152 and flange 164 over the trigger levers 186' and 186, respectively. When the protective sheath 122 penetrates into the anatomical cavity, springs 134 and 172 urge the portal sleeve 116 and protective sheath 122 distally forward causing the protrusion 152 and transverse flange 164 of the protective sheath 122 to bear against trigger levers 186' and 186 in a distal direction to rotate latches 180' and 180 away from portal sleeve extending collar 170' and the transverse flange 140 of the penetrating member 120. With latches 180' and 180 released, extending member 174' operates to move portal sleeve 116 further in a distal direction to the extended position, and retracting member 154 operates to move penetrating member 120 from the extended position to the retracted position shown in FIG. 10. With the tip 138 of the penetrating member 120 safely protected within protective sheath 122 the penetrating unit 114 can be removed from the portal unit 112 leaving the portal sleeve 116 in place for performing various surgical and diagnostic procedures through the lumen thereof.

It will be appreciated that the safety penetrating instrument 110 provides a redundant safety mechanism by at once triggering retraction of the penetrating member and protrusion of the portal sleeve to position the tip of the penetrating member in a protected state. Since either mechanism would suffice for positioning the tip in a protected state, the provision of both mechanisms provides an additional safeguard against malfunction. Additionally, by locating the extending mechanism within the housing and the retracting mechanism within the hub, it is possible to reduce the length of the hub and, therefore, the overall length of the safety penetrating instrument while maintaining a suitable amount of relative movement between the penetrating member and the portal sleeve. While the penetrating member is shown being locked in a fixed position when extended and both the portal sleeve and protective sheath are mounted on spring bias members to move together during penetration, it will be appreciated that the penetrating member could also be mounted within a collar or the like to move proximally during penetration.

Another modification of the safety penetrating instrument of the present invention is shown in FIG. 11, wherein the safety penetrating instrument 210 is similar to the safety penetrating instrument 10 in that penetration of a safety shield through an anatomical cavity wall triggers extension of the safety shield and retraction of the penetrating member, and in addition triggers simultaneous protrusion or extension of the portal sleeve. Penetrating unit 214 for safety penetrating instrument 210 is essentially the same as penetrating unit 14 for safety penetrating instrument 10, including a hub 224 for mounting proximal ends of the penetrating member 220 and safety shield 222 in retracting and extending collars 250 and 270, respectively. A latch 280, similar to latch 80, locks the collars between a pair of pawls 282 and 284 and carries a trigger lever 286 responsive to emergence of the safety shield 22 into the anatomical cavity to release the collars 250 and 270 permitting a retracting member 254 to move the penetrating member 220 from the extended position to the retracted position and an extending member 274 to move the safety shield from the retracted position to the extended position shown in FIG. 12. Portal unit 212 for safety penetrating instrument 210 is essentially the same as portal unit 112 for safety penetrating instrument 110, and includes a housing 218 mounting the proximal end of the portal sleeve 216 between walls of an extending collar 270', similar to extending collar 170', that is locked against distal movement by a latch 280' similar to latch 180', against a distal bias of a second extending member 274' similar to extending member 174'. A protrusion 252 similar to protrusion 152 in safety penetrating instrument 110, is formed intermediate proximal and distal ends of the safety shield 222 so as to be located between the pawl 284' at the distal end of latch 280' and the trigger lever 286' carried by the latch 280' when the penetrating member 220 is extended as shown in FIG. 11.

It will be appreciated that when the safety penetrating instrument 210 is used in the manner previously described in connection with safety penetrating instruments 10 and 110, penetrating member 220, portal sleeve 216 and safety shield 222 will move together during penetration of the anatomical cavity wall, causing all three members to be moved proximally, with protrusion 252 and safety shield flange 264 assuming positions proximally of trigger levers 286' and 286, respectively. Penetration of safety shield 222 into the anatomical cavity then results in distal movement of the safety shield to cause rotation of latches 280' and 280 thereby releasing the retracting mechanism and two extending mechanisms to simultaneously move the penetrating member from the extended position to the retracted position and the portal sleeve and safety shield from their retracted positions to the extended positions shown in FIG. 12.

The safety penetrating instrument 310 illustrated in FIG. 13 includes a penetrating unit 314 having a hub 324 mounting a latch 380 similar to latch 80 in the embodiment of FIG. 1 with the exception that the trigger lever 386 extends transversely from a position on latch 380 so as to be proximal the transverse flange 340 of the penetrating member 320 when the penetrating member is in the extended position shown in FIG. 13. All other features of the safety penetrating instrument 310 being substantially identical to those described for safety penetrating instrument 10, it will be appreciated that the safety penetrating unit 310 operates in the same manner with the exception that penetration of the penetrating member 320 into the anatomical cavity, rather than the safety shield 322, triggers simultaneous retraction of the penetrating member 320 from the extended position shown in FIG. 13 to the retracted position shown in FIG. 14, and extension of the safety shield 322 from the retracted position shown in FIG. 13 to the extended position shown in FIG. 14.

The latch 380 is also shown carrying a third pawl 385 spaced distally from the distal pawl 384 to engage the safety shield extending collar 370 when the safety shield 322 is moved to the extended position shown in FIG. 14, thus preventing proximal movement of the safety shield 322 and exposure of the penetrating member distal end upon withdrawal of the penetrating unit 314. The proximal end of the latch 380 includes an arcuate portion 387 for cradling a control button 389. The control button 389 is mounted in the hub 324 and has a small diameter end received in a socket extending from the bottom wall of the hub, as illustrated and described in Applicant's copending patent application, Ser. No. 08/083,220, filed Jun. 24, 1993, the disclosure of which is incorporated herein by reference. The other end of the control button protrudes from the top wall of the hub to allow longitudinal movement of the control button, and the control button includes a tapered portion contacting the arcuate portion 387 of latch 380. Consequently, depressing the control button moves the latch from the locked position shown in FIG. 13 to a released position such as that shown in FIG. 6 so that movement of the safety penetrating instrument to the protected state shown in FIG. 14 can be manually triggered. The control button 389 can also be used to release the safety shield extending collar 370 from being locked by third pawl 385, thus allowing the safety shield to be retracted and the penetrating member to be extended prior to use. Also shown for purposes of illustration is a leaf spring 393 held in compression between a side wall of the hub 324 and the latch 380 to bias the latch clockwise toward the collars 350 and 370.

FIG. 15 illustrates another modification of the safety penetrating instrument, wherein the modified safety penetrating instrument 410 is responsive to penetration of the penetrating member into an anatomical cavity to trigger simultaneous retraction of the penetrating member and extension of the portal sleeve to place the safety penetrating instrument in the protected state shown in FIG. 16. The safety penetrating instrument 410 is similar to the safety penetrating instruments previously described, having a hub 424 mounting the proximal ends of a protective sheath 422 and a penetrating member 420, a housing 418 mounting the proximal end of a portal sleeve 416, and a retracting collar 450 disposed within the hub 424 and having a proximal wall 446 defining an opening for allowing passage of a guide tube 442 extending from the rear wall 444 of the hub 424, and a distal wall 448 defining an opening for allowing passage of the body of the penetrating member 420 which fits telescopically over the guide tube 442. A latch 480, similar to latch 80, holds the retracting collar 450 and thus the penetrating member 420 in the extended position, a retracting member 454 being held in compression between the collar 450 and the front wall of the hub 424. A second latch 480' extends distally from the rear wall 419 of the housing 418 and has a distal pawl 484' extending through a slot 487 formed at the proximal end of the portal sleeve 416 to maintain the portal sleeve 416 in the retracted position. A portal sleeve extending member 474' is held in compression between the transverse flange 428 at the proximal end of the portal sleeve 416 and the rear wall 419 of the housing 418.

In the embodiment shown, the portal sleeve proximal end is not mounted on a spring within a collar, such as collar 170 in the embodiment of FIG. 8, and the proximal end of the protective sheath 422 is fixedly secured to the front wall of the hub 424, so that neither the portal sleeve 416 nor the protective sheath 422 exhibits any proximal movement during penetration of an anatomical cavity wall. The proximal end of the penetrating member 420 is mounted within a collar 450 and is thus able to retract proximally a predetermined distance against compression of a spring 452 during penetration of the anatomical cavity wall prior to penetrating into the cavity and being biased distally forward by spring 452 to trigger the release of latches 480 and 480' and thus movement of the portal sleeve 416 and the penetrating member 420 into the protected state shown in FIG. 16.

In order to utilize movement of the penetrating member 420 to trigger release of the latch 480' in the housing 418, a third latch 480" extends distally from the rear wall of the hub 424 through the guide tube 442 and terminates distally within the housing 418. The latch 480" includes a generally straight elongate arm 481" having a proximal end pivotably mounted on a pin 433 secured to the rear wall 444 of the hub 424. A latching protrusion or pawl 482" is carried or formed near the proximal end of the arm 481" and extends perpendicularly from the arm 481" through a slot 491 in the guide tube 442 to bear against the proximal wall 446 of the penetrating member retracting collar 450 in the extended position to redundantly lock the collar 450 in the extended position. A transverse protrusion 483" is carried or formed at a distal end of the arm 481" facing the distal pawl 484' of the second latch 480' through aligned slots 487 formed in the guide tube 442, penetrating member 420, protective sheath 422 and portal sleeve 416. A torsion spring (not shown) is connected between the pin 433 and the latch arm 481" to bias the latch 480" clockwise looking at FIG. 15. A trigger arm 486" is rotatably mounted at a distal end of the arm 481" and is biased in a counterclockwise direction looking at FIG. 15 to extend at a slight angle relative to the latch arm 481" and to bear against a nub 493" formed on the arm 481" while being rotatable in a clockwise direction. A protrusion 485" is formed on an internal surface of the penetrating member 420 and is spaced distally of the trigger arm 486" for engaging the trigger arm 486' to cause clockwise rotation thereof when the penetrating member 420 is moved in a proximal direction during penetration, and to rotate the trigger arm 486" counterclockwise against nub 493" when the penetrating member 420 is moved distally upon penetrating into the anatomical cavity. Latch 480" is thus rotated away from the penetrating member retracting collar 450 and towards the distal pawl 484' of the second latch 480' to urge the pawl 484' out of engagement with flange 428 to unlock the penetrating member retracting mechanism and the portal sleeve extending mechanism simultaneously.

It will be appreciated that the safety penetrating instrument 410 provides redundant safety by providing dual latching mechanisms for locking the retracting mechanism to prevent premature retraction of the safety penetrating member 420 during penetration of the anatomical cavity wall. Additionally, it will be appreciated that the extending mechanism for causing the portal sleeve to protrude could also make use of an extending collar, such as the extending collar 170 in the embodiment shown in FIG. 8, and further allow proximal movement of the protective sheath against a distal bias so that all three members move together during penetration of the cavity wall. With the portal sleeve and the protective sheath fixed in the retracted position shown in FIG. 15, however, the tapered distal portion of the penetrating member 420 will normally protrude a predetermined amount in the extended position as shown in FIG. 15 so that during penetration into the anatomical cavity wall, contact with the tissue of the wall will cause proximal movement of the penetrating member 420 to cause alignment of the proximal end of the tapered portion with the distal ends of the portal sleeve and protective sheath.

Another modification of the safety penetrating instrument of the present invention is shown in FIG. 17, wherein the safety penetrating instrument 510 is similar to the safety penetrating instrument 210 shown in FIG. 11, except that the penetrating member, not the safety shield, triggers simultaneous retraction of the penetrating member and protrusion of both the portal sleeve and safety shield. The penetrating and portal units 514 and 512 of safety penetrating instrument 510 are essentially identical to units 114 and 112 shown in FIG. 11, but with the penetrating member 520 carrying a protrusion 531 for performing the triggering function. The penetrating member 520 and safety shield 522 of the safety penetrating instrument 510 have slots 521 and 523 formed intermediate their proximal and distal ends and opening into the housing 518. A generally Y-shaped lever arm 525 has a relatively short stem 533 pivotably suspended intermediate its length on a pin 535 secured to an internal surface of the penetrating member 520, a distal arm 537 extending at an angle from the stem 533 and carrying the protrusion 531 at a distal end in a manner to extend the protrusion through the slots 521 and 523 to engage the trigger lever 586' carried on the latch 580' holding the portal sleeve extending collar 570' in the retracted position, and a proximally extending arm 539 that terminates proximally in an arcuate portion 527 that cradles a pin 529 traversing the inside surface of the guide tube 542 to prevent counterclockwise rotation of the lever 525 looking at FIG. 17 beyond a predetermined position so that when the distal protrusion 531 engages the trigger 586' in a distal direction, the reaction force will not cause rotation of the lever 525 out of engagement with the trigger lever 586'. A torsion spring (not shown) is connected between the pin 533 and the lever arm 525 to normally bias the lever arm 525 in the counterclockwise direction while permitting clockwise rotation. As a result, distal movement of the penetrating member 520 after proximal movement during penetration of the anatomical cavity wall, will trigger simultaneous retraction of the penetrating member 520 and protrusion of the portal sleeve 516 and safety shield 522 to protect the tip of the penetrating member as shown in FIG. 18. Although a lever arm is shown being carried within the penetrating member to trigger extension of the portal sleeve, it will be appreciated that any suitable latching and releasing mechanism can be used, including the use of the latch as described together with a protrusion integrally formed on the body of the penetrating member to protrude through one or more slots in the safety shield. It will also be appreciated that the pin 529 restraining counterclockwise rotation of the lever 525 could be a control button of the type previously described as having a tapered portion to allow the user to manually rotate the lever clockwise looking at FIG. 17 to retract the protrusion 531 into the penetrating member; for example, to ease passage of the penetrating member through the housing when mating the hub to the housing.

A further modification of the safety penetrating instrument is shown in FIG. 19, wherein the safety penetrating instrument 610 is similar to the safety penetrating instrument 10 except that the latch 680" extends distally from the rear wall 644 of the hub 624 within the guide tube 642 and penetrating member 620. The latch 680" includes a generally straight elongate arm 681" having a proximal end pivotably mounted on a pin 683" secured to the rear wall 644 of the hub 624, a pair of spaced latching protrusions or pawls 682" and 684" formed near the proximal end of the latch arm and extending through slots 685 and 687 in the guide tube 642, penetrating member 620 and safety shield 622 to engage safety shield extending and penetrating member retracting collars 670 and 650 mounting proximal ends of the safety shield 622 and penetrating member 620, respectively, and a camming protrusion 686" formed at the distal end of the arm 681" and extending through slots 691 in the penetrating member 620 and safety shield 622 to protrude inside the housing 618. A torsion spring (not shown) is connected between the pin 683" and the latch arm 681" to bias the latch 680" in a counterclockwise direction looking at FIG. 19 so that the latch distal end normally bears against the inside surface of the guide tube. A lever 693 is pivotably mounted within the housing 618 on a pin 694 secured to the walls of the housing or a structure supported in the housing and is rotatable about the pin 694 to cam the latch 680" inwardly into the penetrating member 620 to release the collars 650 and 670. The portal sleeve 616 carries a proximal-facing tab 695 with an angled proximal edge to rotate the lever 693 counterclockwise away from the protrusion 686" when traveling in a proximal direction during penetration of an anatomical cavity wall, and with a transverse distal edge to mate with the lever 693 when the tab 695 travels back in a distal direction upon emergence of the portal sleeve 616 into the anatomical cavity. The lever 693 is thus rotated clockwise, camming the distal latch protrusion 686' inward through slots 691 formed in the safety shield and penetrating member to cause clockwise rotation of the latch 680' and release of the safety shield extending collar 670 and penetrating member retracting collar 650. It will therefore be appreciated that movement of the portal sleeve operates to trigger simultaneous retraction of the penetrating member and protrusion of the safety shield to place the tip of the penetrating member in the protected state shown in FIG. 20. It will also be appreciated that the locking mechanism in safety penetrating instrument 610 is incorporated almost entirely within the guide tube and penetrating member, leaving additional space within the hub and housing which may be used for other mechanisms or done away with to reduce the overall size of the instrument.

The safety penetrating instrument 710 illustrated in FIG. 21 is similar to the safety penetrating instrument 110 shown in FIG. 8, except that the proximal end of the penetrating member is mounted by a retracting collar allowing proximal movement of the penetrating member during penetration of the anatomical cavity wall, and simultaneous retraction of the penetrating member and protrusion of the portal sleeve is triggered by penetration of the portal sleeve into an anatomical cavity. Like the latch 680" for safety penetrating instrument 610, the latch 780" holding the penetrating member retracting collar 750 in the safety penetrating instrument 710 extends distally within the guide tube 742 and penetrating member 720 and includes a generally straight arm 781" having a proximal end pivotably mounted on a pin 783" secured to the rear wall 744 of the hub 724, but unlike latch 680", latch arm 781" carries only a single latching protrusion or pawl 782" near the proximal end of the latch arm 781" and extending through a slot 785 in the guide tube 742 to engage the penetrating member retracting collar 750. The distal end of the latch arm 781' carries a second protrusion 786" extending through aligned slots 691 in the guide tube 642, penetrating member 620 and safety shield 622 to protrude into the housing 618. Like the portal sleeve flange 628, the transverse flange 728 of portal sleeve 716 carries a proximally extending tab 795; however, instead of engaging a lever to cam the protrusion, the tab 795 is configured to engage protrusion 786" directly to cam the latch 780" inwardly to release the retracting collar 750; however, the latch 780" can also be manually released by depression of control button 789, which is similar in structure and function to control button 389 but which extends through the guide tube 742 to contact the latch 780". A second latch 780', similar to latch 180' in the embodiment shown in FIG. 8, is operative to release the portal sleeve extending collar 770' mounting the portal sleeve 716 in response to movement of the portal sleeve 716 under the distal bias of spring 734. While a latch 780" is shown for locking and releasing the retracting collar 750, it will be appreciated that any other suitable locking and releasing mechanism can be used, including the latch and lever mechanism illustrated in FIG. 19.

Yet another modification of the safety penetrating instrument of the present invention is illustrated in FIG. 23, wherein the modified safety penetrating instrument 810 is similar to the safety penetrating instrument 210 except that penetration of the portal sleeve into an anatomical cavity, rather than the safety shield, triggers simultaneous protrusion of the portal sleeve and safety shield. Further, in the safety penetrating instrument 810, penetration of the penetrating member into the anatomical cavity itself triggers retraction of the penetrating member. The portal sleeve 816 and safety shield 822 of safety penetrating instrument 810 are telescopically interfitted so that their respective proximal flanges 828 and 864 are mounted by a single extending collar 870' within the housing 818. The portal sleeve flange 828 forms a distal face for triggering release of the latch 880' holding the extending collar 870' in response to movement of the portal sleeve 816 under the distal bias of a spring 834 held in compression between the safety shield flange 864 and the proximal wall 866' of the extending collar 870' upon emergence of the portal sleeve into the anatomical cavity.

The proximal end of the penetrating member 820 is mounted by a retracting collar 850 in the hub 824 held by a latch 880, similar to latch 480, and the penetrating member flange 840 is movable within the collar 850 to trigger release of the latch 880 to cause retraction of the penetrating member under the influence of retracting member 854. Hence, it will be appreciated that the safety penetrating instrument 810 is responsive to movement of the portal sleeve to trigger simultaneous protrusion of the portal sleeve and safety shield, and to movement of the penetrating member to trigger retraction of the penetrating member, the combination of movements operating to place the tip of the penetrating member in the protected state shown in FIG. 24. It will also be appreciated that the safety penetrating instrument 810 assumes a protected position in response to multiple independent triggers as a further method of ensuring safe operation. The instrument can also be triggered in response to movement of a single member, such as the portal sleeve, by replacing the latch 880' with a lever, such as lever 680", mounted within the guide tube 842 and penetrating member 820 to provide triggered retraction of the penetrating member in response to movement of the portal sleeve of the safety penetrating instrument 810.

FIG. 25 illustrates another modification of the safety penetrating instrument of the present invention wherein the modified safety penetrating instrument 910 is similar to the safety penetrating instruments 10 and 310, but has two trigger levers 986 and 987 carried on the latch 980, trigger lever 986 being disposed for engaging the safety shield flange 964 and the trigger lever 987 being disposed for engaging the penetrating member flange 940. Thus, it will be appreciated that the safety penetrating instrument 910 is responsive to movement of either or both of the penetrating member 920 and the safety shield 922 upon entering an anatomical cavity to trigger simultaneous retraction and protrusion of the penetrating member and safety shield, respectively and to place the tip of the penetrating member in the protected state shown in FIG. 26.

A modification of the safety penetrating instrument is illustrated in FIG. 27 wherein the modified safety penetrating instrument 1010 is similar to the safety penetrating instrument 110 shown in FIG. 8, with the exception that penetration of either or both of the protective sheath 1022 and the penetrating member 1020 into an anatomical cavity triggers retraction of the penetrating member 1020, and penetration of the penetrating member alone also triggers simultaneous protrusion of the portal sleeve 1016 to place the safety penetrating instrument in the protective state shown in FIG. 28. Additionally, since the portal sleeve proximal end 1028 is mounted by a retracting collar 1070', the protective sheath 1022 is mounted on bias member 1072 and the proximal end 1040 of the penetrating member 1020 is mounted by a retracting collar 1050, all three of the penetrating member 1020, portal sleeve 1016 and protective sheath 1022 can move together during penetration of the anatomical cavity wall. Distal movement of the penetrating member 1020 upon punching through the anatomical cavity wall triggers release of the latch 1080' holding the portal sleeve extending collar 1070' mounting the portal sleeve proximal end 1028 by means of a protrusion 1031 carried at the distal end of a lever 1025, similar to lever 525 in the safety penetrating instrument 510 illustrated in FIG. 17. While a lever 1025 is illustrated for triggering release of the latch 1080' holding the portal sleeve extending collar 1070', it will be appreciated that other mechanisms, such as the integral protrusion 152 in FIG. 9, can be formed directly on or carried by the body of the penetrating member, protective sheath, or both, to engage the trigger lever 1086' of the latch 1080'.

Still another modification of the safety penetrating instrument of the present invention is illustrated in FIG. 29, wherein the modified safety penetrating instrument 1110 is similar to the safety penetrating instrument 510 shown in FIG. 17, but has two trigger levers 1186 and 1187 carried on the latch 1180 holding the penetrating member retracting collar 1150 and the safety shield extending collar 1170, the trigger lever 1186 being disposed for engaging the safety shield flange 1164 and the trigger lever 1187 being disposed for engaging the penetrating member flange 1140. A lever 1125, similar to levers 525 and 1025, is suspended within the penetrating member 1020 and protrudes therefrom for engaging the trigger lever 1186' carried on the latch 1180' holding the portal sleeve extending collar 1170' mounting the proximal end of the portal sleeve 1116. It will be appreciated, therefore, that the safety penetrating instrument 1110 is responsive to penetration of either or both of the penetrating member and the safety shield into an anatomical cavity to trigger simultaneous retraction of the penetrating member and protrusion of the safety shield and is responsive to movement of at least the penetrating member to trigger protrusion of both the safety shield and the portal sleeve, achieving the protected state shown in FIG. 30.

Figure 31:
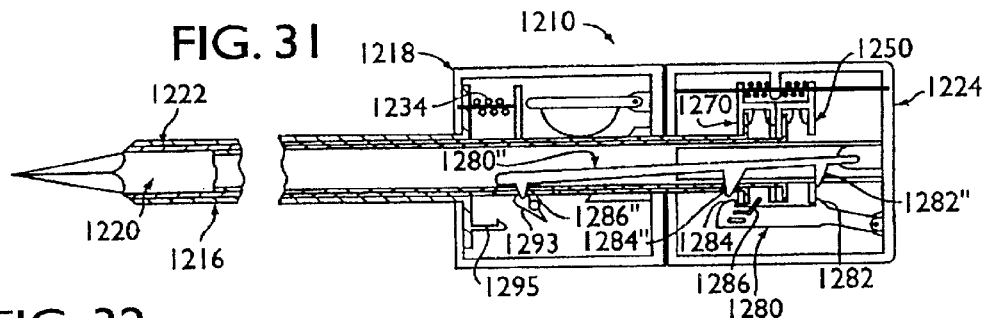
FIG. 31 is a broken side view, partly in section, of still another safety penetrating instrument according to the present invention.
Figure 32:
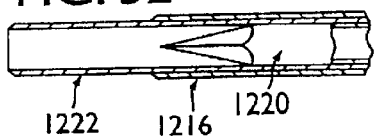
FIG. 32 is a side view, partly in section, showing the distal end of the safety penetrating instrument of FIG. 31 with the tip of the penetrating member in a retracted, protected state.

Another modified safety penetrating instrument 1210 according to the present invention, illustrated in FIG. 31, is similar to the safety penetrating instrument 610 shown in FIG. 19, with the exception that movement of both the safety shield 1222 and portal sleeve 1216, rather than just the portal sleeve 1216, is required to trigger simultaneous retraction of the penetrating member 1220 and protrusion of the safety shield 1222. The redundancy in the locking and releasing mechanism is achieved with a latch 1280, similar to latch 80 in safety penetrating instrument 10, mounted within the hub 1224 to hold the extending and retracting collars 1270 and 1250 mounting the safety shield 1222 and penetrating member 1220, respectively, and carrying a trigger lever 1286 responsive to distal movement of the safety shield 1222 following proximal movement of the safety shield 1222 over the lever 1286 during penetration of the anatomical cavity wall. Thus, it will be understood that the penetrating member retracting collar 1250 and the safety shield extending collar 1270 are held both by latch 1280', which is similar to latch 680' and is responsive to movement of the portal sleeve 1216, and by latch 1280 which is responsive to movement of the safety shield 1222, both of which must be released to place the safety penetrating instrument 1210 in the protected state shown in FIG. 32.

Figure 33:
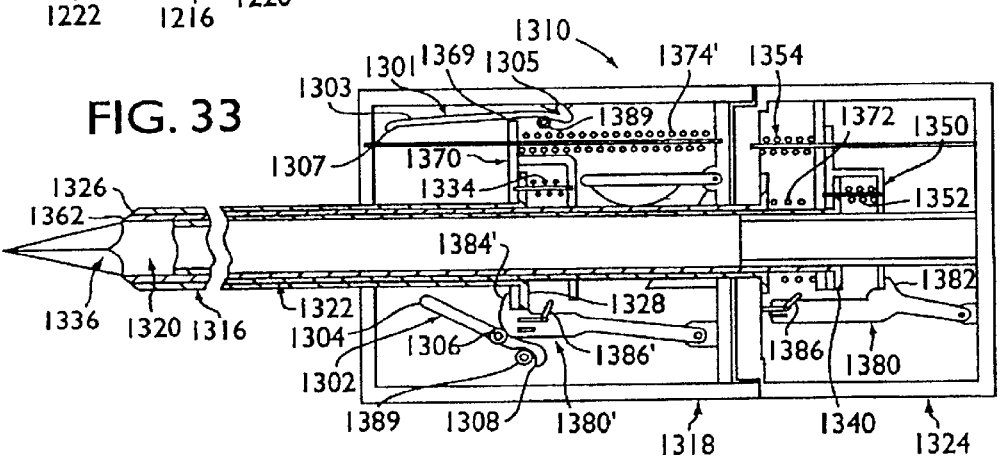
FIG. 33 is a broken side view, partly in section, of yet a further safety penetrating instrument according to the present invention.
Figure 34:
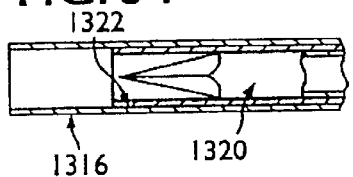
FIG. 34 is a side view, partly in section, of the distal end of the safety penetrating instrument of FIG. 33 showing the tip of the penetrating member in a retracted, protected state.

Safety penetrating instrument 1310, illustrated in FIG. 33, is similar to safety penetrating instrument 110 and is modified such that movement of the portal sleeve 1316 and protective sheath 1322, rather than the protective sheath alone, triggers simultaneous retraction of the penetrating member 1320 and protrusion of the portal sleeve 1316, as shown in FIG. 34. More specifically, the protective sheath 1322 does not carry a protrusion like protrusion 152 in FIG. 8, and the trigger lever 1386' is carried by the latch 1380' proximally of the portal sleeve flange 1328 for being engaged by the flange 1328. Additionally, the penetrating member proximal end 1340 is mounted by a retracting collar 1350, similar to retracting collar 50 in safety penetrating instrument 10, to permit movement of the portal sleeve 1316, protective sheath 1322 and penetrating member 1320 in a proximal direction during penetration of the anatomical cavity wall, thereby maintaining alignment of the chamfered distal ends 1326 and 1362 of the portal sleeve 1316 and protective sheath 1322 with the proximal end of the tapered portion 1336 of the penetrating member 1320. It will be appreciated that retraction of the penetrating member and protrusion of the portal sleeve are independently triggered by movement of the protective sheath and portal sleeve, respectively; however, either one or both of the retracting and protruding functions can be multiply triggered by combining the features of safety penetrating instruments 110 or 710 or both with those described above.

Also illustrated in FIG. 33 are alternative locking elements 1301 and 1302 for locking the extending collar 1370 in the extended position. Locking element 1301 includes a resilient arm 1303 secured at a proximal end 1305 to a side wall of the housing and extending distally at an angle to terminate in a distal tip 1307 spaced a short distance from the front wall of the housing. A control button 1389, similar to control button 389, is positioned to cam the arm 1303 of locking element 1301 toward the side wall mounting the locking element 1301 and away from the collar 1370. In operation, collar 1370 is moved distally under the influence of extending member 1374' and the ridge 1369 of the collar cams the resilient arm 1303 of locking element 1301 toward the side wall and out of the way. When the collar 1370 is fully extended to be in abutment with the front wall of the housing 1318, the arm 1303 of locking element 1301 springs back so that the distal tip 1307 of the arm 1303 bears against the proximal face of the ridge 1369 to prevent proximal movement thereof. The extending collar 1370 can be retracted by depressing the control button 1389 to cam the locking arm 1303 away from the ridge 1369 and by subsequently operating a handle (not shown) such as handle 90 connected to the collar 1370 or portal sleeve 1316 to move along a slot in a proximal direction until the latch 1380' engages the collar 1370 to lock the portal sleeve 1316 in the retracted position shown in FIG. 33.

Locking element 1302 performs the same function as element 1301 and includes a lever arm 1304 mounted centrally on a pin 1306 secured to walls of the housing or a structure supported in the housing. A torsion spring or the like is connected between the pin 1306 and the lever arm 1304 to bias the lever arm clockwise looking at FIG. 33 towards the extending collar 1370 and to lock it in place when extended. A control button 1389 is positioned adjacent the lever proximal end 1308 to prevent clockwise rotation of the locking element 1302 beyond a predetermined point and to facilitate manual release of the locking element by rotating the lever 1304 counterclockwise away from the extending collar 1370.

It will be appreciated that these locking elements can be employed in the hub as well as the housing of any of the safety penetrating instruments described herein to lock extending and/or retracting collars in their protected positions. It will also be appreciated that the locking elements shown are merely exemplary of the types of possible mechanisms and that various other mechanisms, including ball detents and the like, can be used to lock and release the extending and retracting collars of the present invention in extended and retracted positions, respectively.

Figure 35:
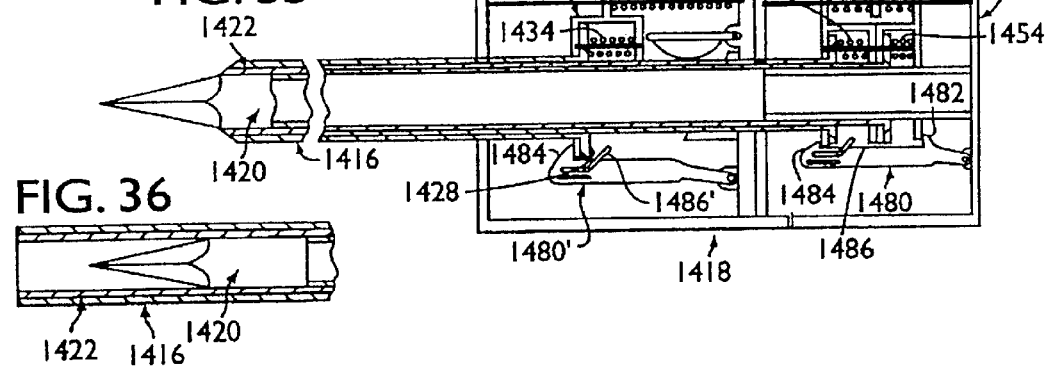
FIG. 35 is a broken side view, partly in section, of another safety penetrating instrument according to the present invention.
Figure 36:
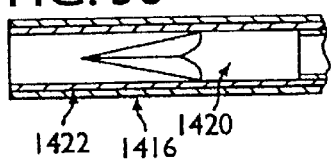
FIG. 36 is a side view, partly in section, of the distal end of the safety penetrating instrument of FIG. 35 showing the tip of the penetrating member in a retracted, protected state.

Another modification of the safety penetrating instrument of the present invention is illustrated in FIG. 35, wherein the modified safety penetrating instrument 1410 is similar to safety penetrating instrument 210 shown in FIG. 11, with the exception that the safety shield 1422 does not carry a protrusion, such as protrusion 152, and the trigger lever 1486', while being similar to trigger lever 186', is carried at a more distal location on the latch 1480' to be engaged by the portal sleeve flange 1428 to trigger release of the extending collar 1470' mounting the proximal end of the portal sleeve 1416. It will appreciated, therefore, that movement of the portal sleeve and safety shield in safety penetrating instrument 1410, as opposed to movement of the safety shield alone in safety penetrating instrument 110, triggers retraction of the penetrating member and simultaneous protrusion of the portal sleeve and safety shield, as shown in FIG. 36. It will also be appreciated that either one or both of the retracting and protruding functions can be multiply triggered by combining the above features with those of safety penetrating instruments 210 or 610 or both.

The safety penetrating instrument 1510 illustrated in FIG. 37 is similar to the safety penetrating instrument 1210 previously described, with the exception that the trigger lever 1586 is disposed more proximally on the latch 1580 to be engaged by the penetrating member proximal flange 1540 rather than the safety shield proximal flange 1564 as in the safety penetrating instrument 1210, and the pivoted latch 1280" mounted within the penetrating member of safety penetrating instrument 1210 is replaced in the safety penetrating instrument 1510 with a resilient clip 1580' having two parallel legs 1583 and 1585 joined by a cross-member 1587 and normally biased apart, leg 1583 being fixed to an inner surface of the penetrating member and leg 1585 being configured to form an arcuate protrusion 1586" extending through slots 1591 formed in the body of the penetrating member 1520 and the safety shield 1522 within the housing 1518 adjacent the lever 1593. Like portal sleeve 1216, portal sleeve 1516 carries on the transverse flange 1528 a proximally extending tab 1595 configured to engage the lever 1593 distally to cause rotation thereof toward the protrusion 1586".

During penetration of the anatomical cavity wall, the penetrating member 1520 and safety shield 1522 move together proximally as a consequence of their being "pinned" together by the protrusion 1586". The portal sleeve 1516 also moves proximally against spring 1534 pushing the tab 1595 past the lever 1593, thereby rotating the lever 1593 counter-clockwise looking at FIG. 37. Lever 1593 like lever 1293, is biased to rotate clockwise toward the protrusion 1586", and presents a distal surface for engaging the tab 1595 when the tab is biased to move distally upon penetration of the portal sleeve 1516 into the anatomical cavity. The distal force applied to the lever 1593 by the tab 1595 causes the lever 1593 to cam the protrusion 1586" towards the interior of the penetrating member 1520, allowing the penetrating member 1520 and safety shield 1522 to move relative to one another. At about the same time, the penetrating member 1520 and safety shield 1522 penetrate through the anatomical cavity wall and are biased distally forward by springs 1552 and 1572, respectively, the penetrating member bearing against the trigger lever 1586 to rotate the latch 1580 away from the retracting and extending collars 1550 and 1570 mounting the penetrating member and safety shield proximal ends to cause retraction and protrusion thereof, respectively.

Thus, it will be appreciated that the safety penetrating instrument 1510 is responsive to movement of both the portal sleeve and penetrating member to trigger retraction of the penetrating member and protrusion of the safety shield, so that triggering will not occur inadvertently before the portal sleeve penetrates completely through the anatomical cavity wall. It will also be appreciated that any structure carrying a protrusion biased to protrude through openings in the penetrating member and safety shield can be used and that other mechanisms, such as latch 1280' for safety penetrating instrument 1210, can be employed in conjunction with or in lieu of the clip to achieve redundant locking in safety penetrating instrument 1510.

A further modification of the safety penetrating instrument of the present invention is illustrated in FIG. 39, wherein the modified safety penetrating instrument 1610 is similar to the safety penetrating instrument 1310 previously described and shown in FIG. 33, with the exception that the trigger lever 1686, while being similar to trigger 1386, is located proximally of the penetrating member flange 1640 when the penetrating member 1620 is in the extended position shown in FIG. 39. Hence, the safety penetrating instrument 1610 is responsive to movement of the portal sleeve 1616 to trigger protrusion of the portal sleeve 1616 and to movement of the penetrating member 1620 to trigger retraction of the penetrating member 1620, the combined effect of which places the tip of the penetrating member in the protected state shown in FIG. 40. It will be appreciated, however, that redundant locking can also be provided by mounting a latch such as latch 780", within the penetrating member for coupling movement of the penetrating member and portal sleeve to release the internal latch. Similarly, redundant triggering can be achieved by substituting the latch 1680 with an internal latch, such as latch 780", and providing a trigger lever at the distal end of the latch for engagement by a protrusion formed on the internal wall of the penetrating member, as shown in FIG. 15.

Yet another modification of the safety penetrating instrument of the present invention is illustrated in FIG. 41, wherein the modified safety penetrating instrument 1710 is similar to the safety penetrating instrument 1410 previously described and shown in FIG. 35, with the exception that the trigger lever 1786, while being similar to trigger lever 1486', is located proximally of the penetrating member flange 1740 when the penetrating member 1720 is in the extended position shown in FIG. 41. As a result, the safety penetrating instrument 1710 is responsive to penetration of the portal sleeve 1716 into the anatomical cavity to trigger protrusion of the portal sleeve 1716 and to penetration of the penetrating member 1720 into the anatomical cavity to trigger simultaneous protrusion of the safety shield 1722 and retraction of the penetrating member 1720, the combined effect of which places the tip of the penetrating member in the protected state shown in FIG. 42. It will be appreciated, however, that in addition to the aforementioned mechanisms, any suitable mechanism for triggering release of the portal sleeve in response to movement of the penetrating member can be added for additional safety, as can any suitable mechanism for releasing the latch 1780' in response to movement of the portal sleeve.

Still another modification of the safety penetrating instrument of the present invention is illustrated in FIG. 43, wherein the modified safety penetrating instrument 1810 is similar to the safety penetrating instrument 1510 previously described and shown in FIG. 37, with the exception that two trigger levers 1886 and 1887 are carried on the latch 1880, trigger lever 1886 being disposed for engaging the safety shield flange 1864 and trigger lever 1887 being disposed for engaging the penetrating member flange 1840. Thus, it will be appreciated that the safety penetrating instrument 1810 is responsive to movement of the portal sleeve 1816 and penetrating movement of either one or both of the penetrating member 1820 and the safety shield 1822 to trigger simultaneous retraction of the penetrating member 1820 and protrusion of the safety shield 1822, as shown in FIG. 44. It will be appreciated, however, that redundant locking can be achieved by providing, in addition to or in lieu of the clip 1880', any other mechanism suitable for holding the retracting and extending collars mounting the penetrating member and safety shield, respectively, and being responsive to movement of the portal sleeve for triggering release thereof.

The modified safety penetrating instrument 1910, illustrated in FIG. 45, is similar to the safety penetrating instrument 1610 previously described and shown in FIG. 39, with the exception that the latch 1980 extends further distally towards the transverse flange 1964 of the protective sheath 1922 and carries a second trigger lever 1986 for engaging the protective sheath flange 1964. It will be appreciated, therefore, that the safety penetrating instrument 1910 is responsive to penetrating movement of the portal sleeve 1916 to trigger protrusion of the portal sleeve 1916, and is responsive to penetrating movement of either or both of the penetrating member 1920 and protective sheath 1922 to trigger retraction of the penetrating member 1920, the combined effect of which is to place the tip of the penetrating member 1920 in the protected state shown in FIG. 46. It will also be appreciated, however, that redundant locking can be achieved by providing, in addition to the mechanisms previously described, any suitable mechanism for locking and releasing the portal sleeve in response to movement of either or both of the protective sheath and penetrating member. Similarly, any of the mechanisms previously described for releasing the penetrating member in response to movement of the portal sleeve can be employed.

The safety penetrating instrument of the present invention can be modified as shown in FIG. 47, wherein the modified safety penetrating instrument 2010 is similar to the safety penetrating instrument 1710 previously described and illustrated in FIG. 41, and further includes a second trigger lever 2086 carried on the latch 2080, the second trigger 2086 being disposed for engaging the safety shield flange 2064. As a result, the safety penetrating instrument 2010 is responsive to movement of the portal sleeve 2016 to trigger protrusion of the portal sleeve 2016, and to movement of either or both of the penetrating member 2020 and the safety shield 2022 to trigger retraction of the penetrating member 2020 and simultaneous protrusion of the safety shield 2022, thereby moving the tip of the penetrating member into the protected state shown in FIG. 48. It will be appreciated, however, that redundant locking can be achieved with any suitable mechanisms for holding and releasing the retracting and extending collars mounting the penetrating member and safety shield, respectively, in response to movement of the portal sleeve, and/or with suitable mechanisms for holding and releasing the extending collar mounting the portal sleeve, in response to movement of either or both of the safety shield and the penetrating member. Similarly, redundant triggering is possible by carrying a second trigger lever on the latch engaging the portal sleeve and mounting a latch internally of the penetrating member such as the latch shown in FIG. 29, for triggering extension of the portal sleeve in response to movement of one or all of the portal sleeve, penetrating member and safety shield.

Only the penetrating unit 2114 of the modified safety penetrating instrument 2110 has been illustrated in FIG. 49; however, it will be appreciated that the portal unit can be formed with any cooperating structure and is particularly advantageous when utilized with the automatically protruding portal sleeve mechanism shown in FIG. 47, for example. The penetrating unit 2114 of the safety penetrating instrument 2110 includes a hub 2124 mounting proximal ends of the safety shield 2122 and penetrating member 2120 in extending and retracting collars 2170 and 2150, respectively. The collars 2170 and 2150 are locked in place by a lever 2180" pivotally mounted on a pin 2181" secured to the guide tube 2142 intermediate proximal and distal ends of the lever 2180". The lever 2180" includes a pair of generally parallel arms 2183' and 2189" disposed on opposite sides of the pin 2181" and connected by a cross-member 2193" mounted on the pin 2181". A torsion spring of the like is connected between the pin 2181" and the cross-member 2193" to bias the lever 2180" clockwise looking at FIG. 49. Leg 2183" extends proximally from the cross-member and carries a pair of spaced pawls 2182" and 2184" that extend through the guide tube 2142, penetrating member 2120 and safety shield 2122 to engage and lock the collars 2150 and 2170, and leg 2189" extends distally from the cross-member and terminates in single pawl 2186" having an angled distal edge. A proximal-facing tab 2185" is suspended from an internal wall of the penetrating member 2120 and is spaced distally of the distal pawl 2186" of the lever 2180" when the penetrating member 2120 of the safety penetrating instrument 2110 is in the extended position shown in FIG. 49. The tab 2185' terminates proximally in a proximal end 2187" having a slanted proximal or leading edge 2188" for slidingly contacting the angled distal edge of distal pawl 2186" and, a vertical or transverse abutment surface 2191" for mating with the pawl 2186". Both the penetrating member 2120 and safety shield 2122 are biased distally within their respective collars 2150 and 2170, while being able to move proximally a predetermined distance during penetration of the anatomical cavity wall. As a result, proximal movement of the penetrating member 2120 causes the tab 2185" to be guided over and to mate with the distal pawl 2186" of the lever 2180" so that upon movement of the penetrating member 2120 in a distal direction after penetrating the anatomical cavity wall, tab 2185" pulls the distal lever arm 2189" of lever 2180" causing rotation of the lever 2180' in a counter-clockwise direction looking at FIG. 49 releasing the retracting and extending collars 2150 and 2170 to cause retraction of the penetrating member 2120 and protrusion of the safety shield 2122. It will be appreciated that by mounting the locking and releasing mechanism within the guide tube and penetrating member, the hub 2124 can be made smaller to reduce cost and achieve other benefits. The lever 2180" can be configured in any suitable manner to convert the distal movement of the tab to rotate or retract the proximal arm of the lever away from collars 2150 and 2170, for example by varying the length of the cross-member and/or the manner of attaching the arms.

As mentioned previously, the penetrating member can be constructed of multiple parts, and FIG. 50 illustrates the penetrating unit of another modified safety penetrating instrument 2210 employing a multi-part penetrating member 2220; it being understood that the penetrating unit 2214 can be mated with any cooperating portal unit previously described. The modified safety penetrating instrument 2210 is similar to the safety penetrating instrument 2110 illustrated in FIG. 49, with the exception that the distal end 2236 of the penetrating member 2220 fits telescopically within a tubular body 2221 defining the proximal end of the penetrating member. A bias member in the form of a spring 2223 is held in compression between the tubular body 2221 of the penetrating member and the distal portion 2236 of the penetrating member to allow proximal and distal movement of the distal portion 2236 relative to the tubular body 2221. A locking and releasing mechanism including a lever 2280" similar to lever 2180" described in connection with safety penetrating instrument 2110, is mounted within the guide tube 2242 and penetrating member of the safety penetrating instrument 2210, with the tab 2285" extending proximally from the proximal end of the distal portion 2236 of the penetrating member. As shown, the safety penetrating instrument 2210 is responsive to movement of the distal portion 2236 of the penetrating member 2220 to trigger retraction of the entire penetrating member 2220 and protrusion of the safety shield 2222.

Movement of the safety penetrating instrument of the present invention to a protected state wherein the tip of the penetrating member is retracted and one or both of the portal sleeve and safety shield are extended can also be triggered upon penetration of the safety penetrating instrument into anatomical tissue to a predetermined depth.

Figure 51:
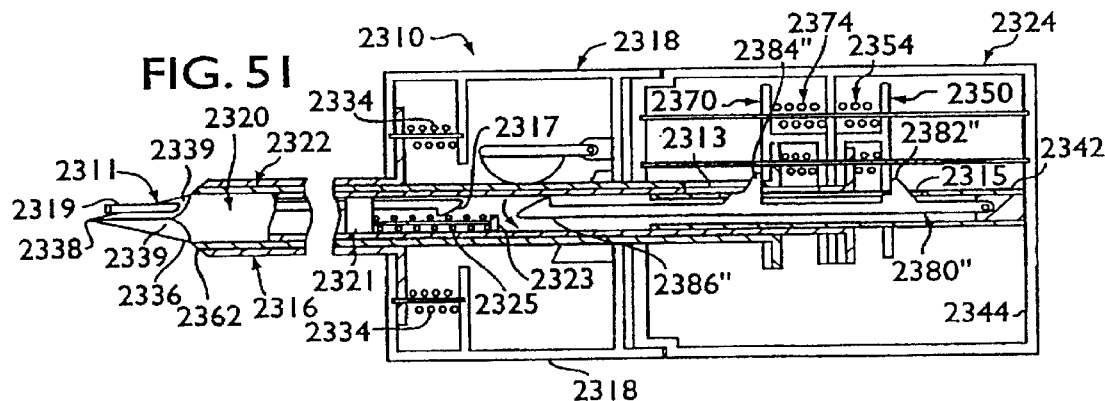
FIG. 51 is a broken side view, partly in section, of a further safety penetrating instrument according to the present invention.

A modified safety penetrating instrument having such capability is illustrated in FIG. 51, wherein the modified safety penetrating instrument 2310 is triggered by movement of a probe 2311 carried by the safety penetrating instrument upon penetration of the safety penetrating instrument into anatomical tissue to a predetermined depth. The modified safety penetrating instrument 2310 includes a penetrating unit 2314 having a hub 2324 mounting proximal ends of a penetrating member 2320 and a safety shield 2322 in retracting and extending collars 2350 and 2370, as described previously in connection with safety penetrating instrument 10. Slots 2313 are formed near proximal ends of the penetrating member 2320 and safety shield 2322 and are aligned in the extended position as shown to extend distally a distance at least equal to the spacing between walls of one of the retracting or extending collars 2350 and 2370. A slot 2315 is also formed in the guide tube 2342 to extend slightly beyond the collars 2350 and 2370 in proximal and distal directions when the collars are gathered together as shown. A spring-biased latch 2380", similar to latch 680", is pivotably mounted on the rear wall 2344 of the hub 2324 so as to extend distally within the guide tube 2342 and includes a pair of spaced transverse protrusions 2382" and 2384" for extending through the slots 2313 and 2315 to engage or lock the retracting and extending collars 2350 and 2370. The latch 2380" terminates distally at a distal end 2386" disposed within the penetrating member 2320 at a point intermediate the length of the housing 2318 of portal unit 2312. The distal end 2386" of the latch 2380" forms a distal-facing angled surface configured for rotating the latch 2380" out of engagement with the collars 2350 and 2370 upon sliding contact with a proximal-facing cam surface. The tip 2338 of the penetrating member 2320 is defined by a number of distally tapering bevels or facets 2339 and the probe 2311 extends longitudinally through an opening in one of the facets to protrude distally alongside the tip 2338 of the penetrating member 2320. The proximal end 2317 of the probe 2311 forms a proximal-facing cam surface distally spaced from the distal end 2386" of the latch 2380" to slidingly contact the distal-facing cam surface thereof upon proximal movement of the probe 2311 a predetermined distance, for example corresponding approximately to the thickness of the anatomical cavity wall to be penetrated. The protruding or distal portion 2319 of the probe 2311 is preferably a rod carried on a cylindrical plug 2321 telescopically fitted within the penetrating member 2320 and positioned distally of a transverse wall 2323 formed on an interior surface of the penetrating member. A spring 2325 is shown being held in compression between the wall 2323 and the plug 2321 to bias the probe 2311 in the distal direction. The proximal end 2317 of the probe 2311 extends proximally from the cylindrical plug 2321 toward the distal end 2386" of the latch 2380".

Figure 52:
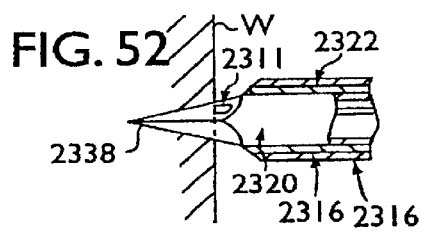
FIG. 52 is a side view, partly in section, of the distal end of the safety penetrating instrument of FIG. 51 showing the probe of the instrument retracted a predetermined proximal distance.

During penetration of an anatomical cavity wall W, the penetrating member 2320, the safety shield 2322 and the portal sleeve 2316 move together through the tissue, the penetrating member 2320 and safety shield 2322 remaining locked in extended and retracted positions, respectively. The probe 2311 is moved proximally relative to the penetrating member 2320 against the distal bias of the spring 2325 due to contact of the probe 2311 with the tissue of the anatomical cavity wall as shown in FIG. 52. Accordingly, the probe 2311 acts as a sensing rod to sense the depth of penetration into the cavity wall W and to obtain predetermined proximal movement of the proximal-facing cam surface 2317 in accordance with the sensed penetration. Movement of the probe 2311 proximally causes proximal movement of the cam surface 2317 within the penetrating member. Once the cam surface 2317 has moved the predetermined proximal distance, it engages the angled surface of the latch distal end 2386" causing the latch 2380" to rotate counterclockwise looking at FIG. 51 and the transverse protrusions 2382" and 2384" to be moved away from the collars 2350 and 2370. The penetrating member 2320 will then move from the extended position shown to a retracted position, and the safety shield 2322 will move from the retracted position shown to an extended position. The tip 2338 of the penetrating member 2320 is thus disposed proximally of the safety shield distal end 2362 in a protected state as described previously in connection with safety penetrating instrument 10, for example. The hub 2324 can then be withdrawn from the housing 2318 leaving the portal sleeve 2316 in place for conducting various procedures via the lumen of the portal sleeve.

By providing a predetermined proximal distance to be in accordance with the thickness of the anatomical cavity wall, retraction of the penetrating member is insured as soon as the penetrating member has been introduced into the anatomical cavity. Additionally, by providing a variety of safety penetrating instruments with different predetermined proximal distances, a safety penetrating instrument can be optimally selected for use in penetrating a particular known or estimated thickness of anatomical tissue to insure retraction of the penetrating member immediately upon introduction of the tapered portion into the anatomical cavity.

Figure 53:
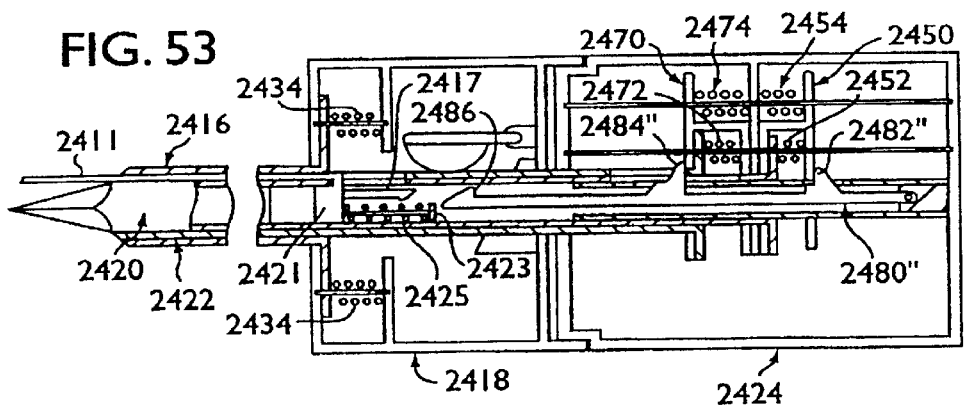
FIG. 53 is a broken side view, partly in section, showing yet another safety penetrating instrument according to the present invention.
Figure 54:
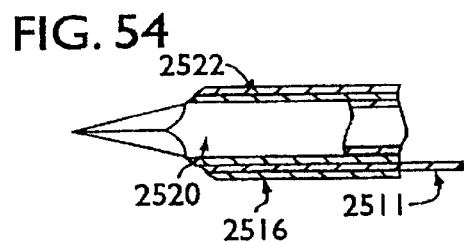
FIG. 54 is a side view, partly in section, of an alternative placement for the probe.
Figure 55:
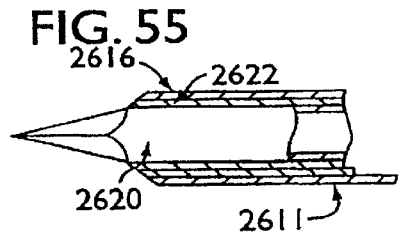
FIG. 55 is a side view, partly in section, showing an additional placement for the probe.

Although the probe 2311 is illustrated in FIG. 51 as extending through a facet 2339 at the distal end 2336 of the penetrating member 2320, movement of the safety penetrating instrument to a protected state can also be triggered by proximal movement of a probe 2411, similar to probe 2311 and disposed between a portal sleeve 2416 and penetrating member 2420 as shown in FIG. 53, by a probe 2511 disposed between a portal sleeve 2516 and safety shield 2522 as shown in FIG. 54, by a probe 2611 alongside a portal sleeve 2616 as shown in FIG. 55, or any combination of probes. Additionally, any suitable mechanism for locking one or all of the portal sleeve, safety shield and penetrating member against the bias of extending or retracting members can be used together with mechanisms suitable for releasing the locked members in response to proximal movement of one or more of the aforementioned probes, such as those described in applicant's copending patent application, Ser. No. 08/177,616, filed Jan. 4, 1994, and applicant's patent application Ser. No. 07/848,838, filed Mar. 10, 1992, the disclosures of which are incorporated herein by reference.

Figure 56:
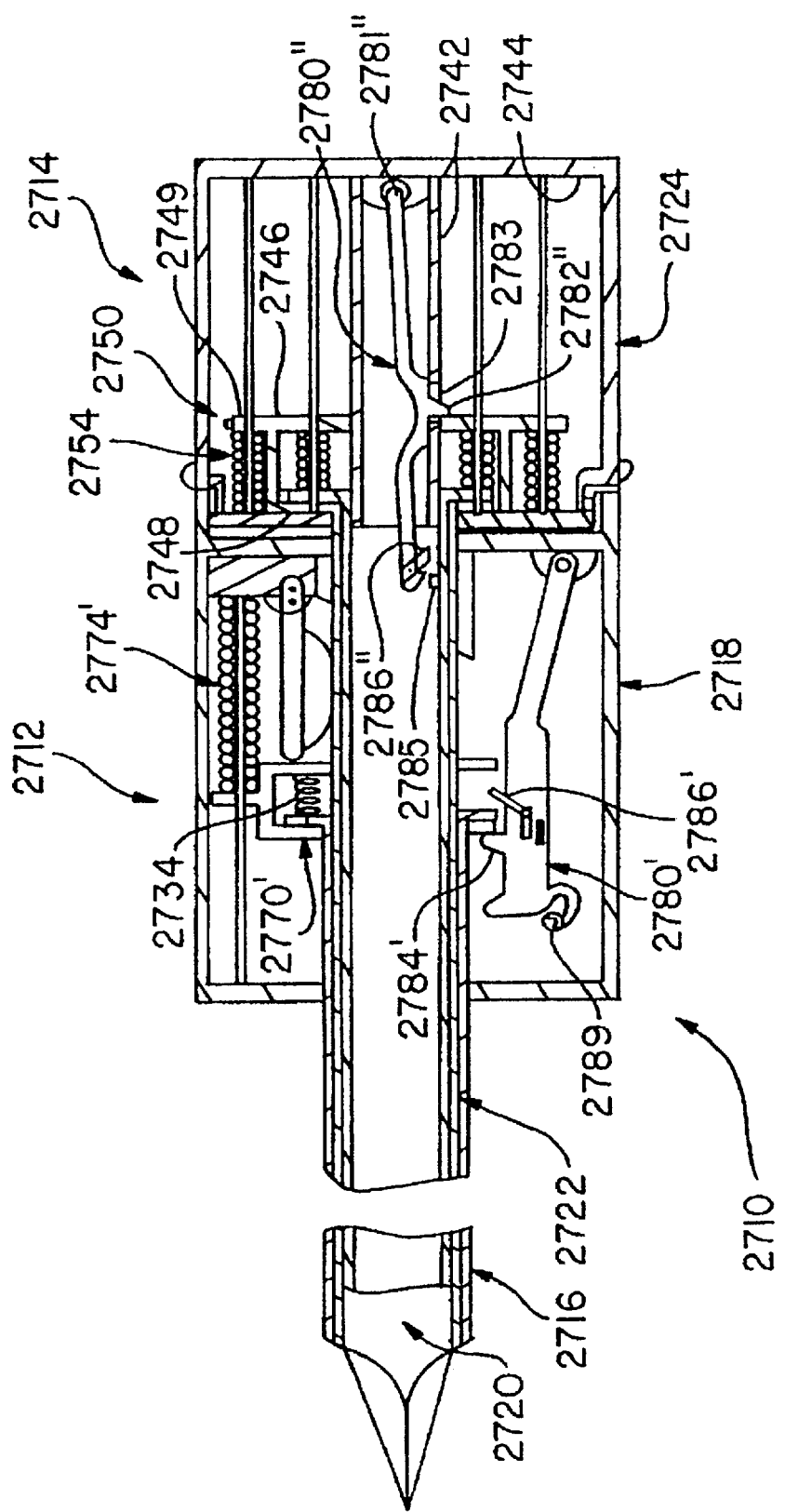
FIG. 56 is a broken side view, partly in section, of still another safety penetrating instrument according to the present invention.

The safety penetrating instrument 2710 illustrated in FIG. 56 is responsive to movement of the portal sleeve 2716 to trigger protrusion of the portal sleeve 2716 and is responsive to movement of the penetrating member 2720 to trigger retraction of both the penetrating member 2720 and the protective sheath 2722. The portal unit 2712 for the modified safety penetrating instrument 2710 includes a portal housing 2718, similar to portal housing 1318 in FIG. 33, mounting the proximal end of the portal sleeve 2716 in an extending collar 2770' lockable with a latch 2780' pivotably supported on a rear wall of the housing 2718 and released by means of a trigger lever 2786' carried on the latch and operative in the manner previously described in connection with latch 80, for example. The penetrating unit 2714 for the modified safety penetrating instrument 2710 mounts the proximal end of the penetrating member 2720 within a retracting collar 2750 having a distal wall 2748 integrally connected with the proximal end of the protective sheath 2722. A spring is held in compression between the proximal wall 2746 of the collar 2750 and a transverse flange 2740 of the penetrating member 2720 to bias the transverse flange 2740 against the proximal wall 2746 of the collar 2750. A retracting member 2754 is also held in compression between the front wall 2741 of the hub 2724 and the ridge 2749 opposite the proximal wall 2746 of the collar 2750. The retracting collar 2750 is locked against the proximal bias of the retracting member 2754 by means of a latch 2780", similar to latch 480", which is pivotably mounted on a pin 2781" secured to the rear wall 2744 of the hub 2724 and extending distally therefrom to engage the proximal wall 2746 of the collar 2750 through a slot 2783 formed in the guide tube 2742. The latch 2780" terminates distally in a distal end carrying a trigger lever 2786" for engaging a protrusion 2785 formed on an interior surface of the penetrating member 2720 to cause rotation of the latch 2780" away from the collar 2750 to trigger retraction thereof. It will be appreciated, therefore, that the penetrating member and portal sleeve of safety penetrating instrument 2710 will move together during penetration of an anatomical cavity wall, and upon introduction of the penetrating member and portal sleeve into the anatomical cavity, the portal sleeve will be moved from the retracted position shown in FIG. 56 to a protruding position, and the penetrating member will be moved, along with the protective sheath, from the extended position shown in FIG. 56 to a retracted position wherein the tip of the penetrating member is spaced proximally of the portal sleeve distal end to be protected.

Figure 57:
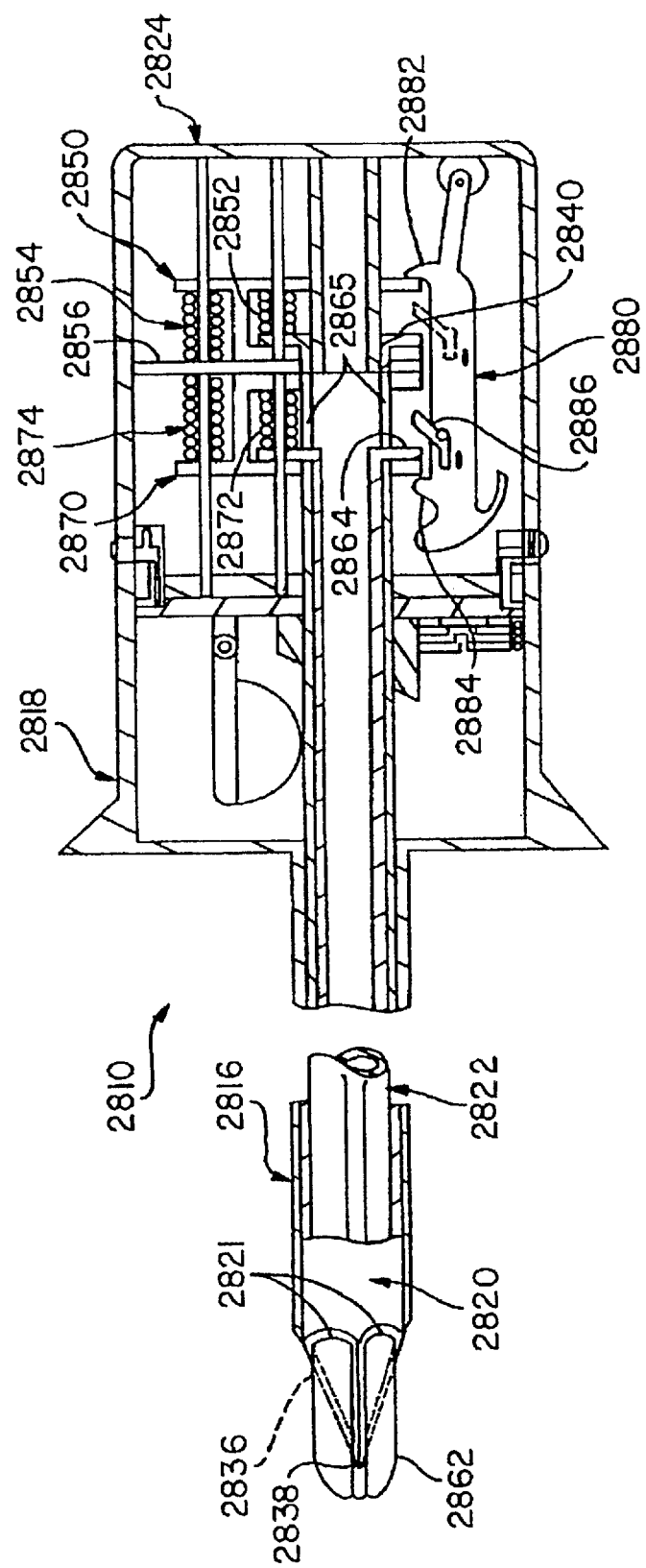
FIG. 57 is a broken side view, partly in section, of yet a further safety penetrating instrument according to the present invention.

In a further modification of the safety penetrating instrument of the present invention, illustrated in FIG. 57, the modified safety penetrating instrument 2810 includes a hollow penetrating member 2820 defining a plurality of apertures 2821 at the penetrating member distal end 2836 and a safety probe 2822 telescopically fitted within the penetrating member 2820 and having a distal end 2862 configured to pass through the apertures 2821 to protrude from the penetrating member distal end 2836. In the extended position, shown in FIG. 57, the safety probe distal end 2862 extends through the apertures 2821 and protrudes distally beyond the tip 2838 of the penetrating member 2820 to protect the tip. The proximal end of the safety probe 2822 includes a transverse flange 2864 extending through slots 2865 formed in the body of the penetrating member 2820 to be mounted within an extending collar 2870. The penetrating member proximal end 2840 is mounted within a retracting collar 2850, and extending and retracting collars 2870 and 2850 are held in a locked position by a latch 2880, similar to latch 80, until such time as the safety penetrating instrument is triggered by penetration of the safety member 2822 into an anatomical cavity.

From the above, it will be appreciated that the safety penetrating instrument of the present invention provides a safe and reliable means for penetrating the anatomical wall of a cavity by simultaneously retracting the penetrating member and extending one or more safety members to assume a protected position wherein the distal tip of the penetrating member is protected and cannot contact anatomical organs and tissue. The safety penetrating instrument is triggered to move to the protected position by movement of an operating member carried by the safety penetrating instrument, which operating member can, for example, be the portal sleeve, a safety shield or safety probe, a protective sheath or protective probe, the penetrating member, a component partially within and around the penetrating member, a predetermined depth probe, or any combination of the foregoing. By providing a safety penetrating instrument having an operating member movable proximally a predetermined distance or movable distally upon penetration into the anatomical cavity to trigger release of one or more safety members to move distally to an extending position while also triggering release of the penetrating member to move proximally to a retracted position, the force biasing the safety members distally can be increased while minimizing the force required to penetrate the anatomical cavity wall. If the safety modes (i.e., protrusion and retraction) are triggered by distal movement of the operating member upon entering the anatomical cavity, the bias force for biasing the operating member distally need only be great enough to produce slight longitudinal movement of the operating member during penetration. Should one of the mechanisms fail to operate properly, the tip of the penetrating member will still be placed in a protected position. Moreover, by combining extension of a safety member mounted by the housing with retraction of the penetrating member mounted by the hub, it is possible to protect the tip of the penetrating member with a reduced amount of travel of the penetrating member in the hub, thereby reducing the size of the hub.

Figure 58:
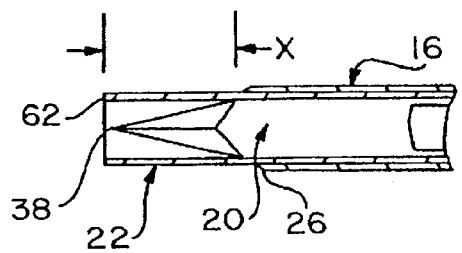
FIGS. 58–67 are side views, partly in section, showing alternative distal configurations for the safety penetrating instrument of the present invention.
Figure 59:
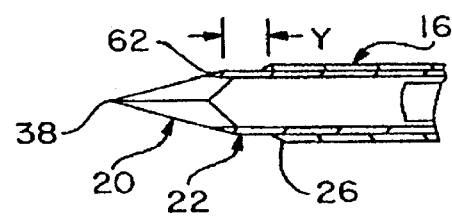
Figure 60:
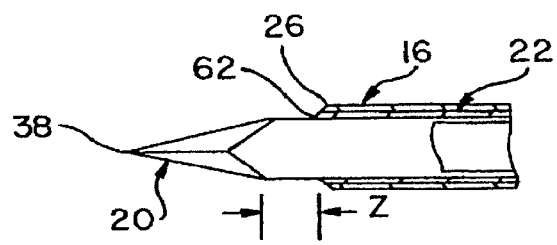
Figure 61:
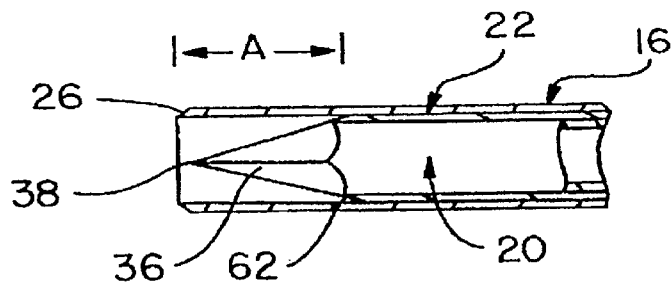

While the portal sleeve and safety shield distal ends have been illustrated and described in certain embodiments as being in alignment with the tapered portion of the penetrating member distal end in the extended state, other configurations can be used, including one in which the distal end 26 of a portal sleeve 16 is aligned with the distal end 38 of a penetrating member 20, and the distal end 62 of a safety shield 22 is spaced distally a predetermined distance X from the portal sleeve distal end 26, as shown in FIG. 58. With the safety shield distal end 62 distally spaced from the portal sleeve distal end 26, it is advantageous to mount the safety shield on a spring or the like to permit proximal movement thereof into alignment with the portal sleeve and penetrating member and to protect the tip of the penetrating member until it has penetrated into anatomical tissue. In FIG. 59, the safety shield distal end 62 is aligned with the penetrating member distal end 38 and the portal sleeve distal end 26 is spaced proximally a predetermined distance Y from the safety shield distal end 62, so that it would be advantageous to mount at least the penetrating member 20 and safety shield 22 on springs or the like to permit proximal movement thereof into alignment with the portal sleeve distal end. Another modified distal configuration is shown in FIG. 60, wherein the portal sleeve and safety shield distal ends 26 and 62 are aligned together and are spaced proximally a predetermined distance Z from the tapered distal end 36 of the penetrating member 20. In this embodiment it is advantageous to mount at least the penetrating member 20 on a spring or the like to permit proximal movement thereof into alignment with the safety shield and portal sleeve distal ends 62 and 26. FIG. 61 illustrates a further modification in which the portal sleeve distal end 26 is distally spaced from the safety shield distal end 62 and penetrating member distal end 36 a predetermined distance A and is preferably mounted on a spring or the like to permit proximal movement of the portal sleeve 16 into alignment with the penetrating member and safety shield distal ends 36 and 62. It will be appreciated that the various distally protruding members can be distally biased to trigger release of any of the foregoing locking mechanisms upon penetrating into an anatomical cavity or can function equally as well as probes triggering release of the locking mechanisms upon penetration of the safety penetrating instrument to a predetermined depth. Moreover, the foregoing distal configurations can be adapted for use with any of the safety penetrating instruments described herein, including those having safety shields, safety probes, or protective sheaths.

Figure 62:
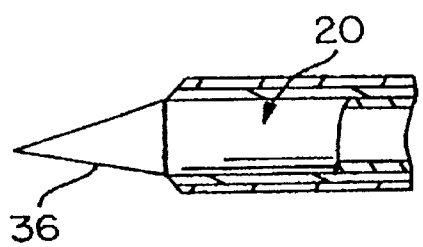
Figure 63:
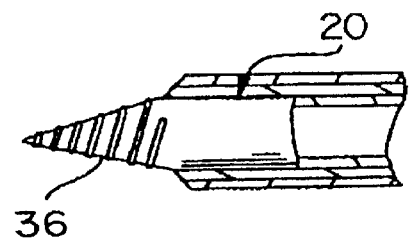
Figure 64:
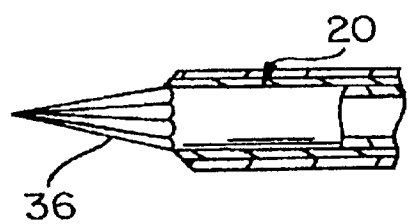
Figure 65:
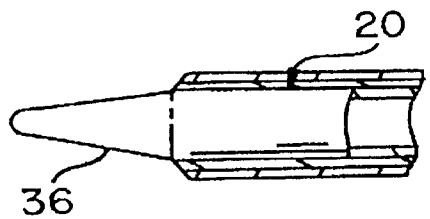
Figure 66:
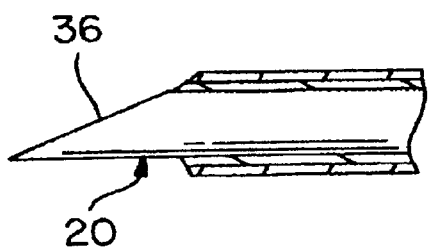
Figure 67:
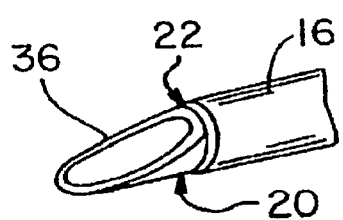

The components of the safety penetrating instrument of the present invention can be made of any suitable, medical grade materials to permit sterilization for reuse or for single patient use. The components can be made of multiple parts or various configurations and materials to reduce cost. The portal unit can have various valves, stop cocks and seals in the housing to control fluid flow of air through various adapters to adjust to the size of the instruments inserted through the portal unit. The penetrating member distal end can have any configuration desired for a particular procedure, for example, the pyramidal trocar configuration shown or a conical distal end 36 (FIG. 62), a threaded distal end 36 (FIG. 63), a multifaceted distal end (i.e., having greater than three facets as shown in FIG. 64), a blunt distal end (FIG. 65), a slanted distal end 36 (FIG. 66) or a hollow needle configuration with fluid flow therethrough (FIG. 67).

With the safety penetrating instrument of the present invention, at least two modes of safety are provided, i.e., retraction of the penetrating member and protrusion of one or more safety members. By "safety member" is meant any structure movable relative to the penetrating member to protect the tip of the penetrating member within an anatomical cavity. Since in the safety penetrating instrument of the present invention one or both of a cannula and a safety shield or probe can be extended to protect the penetrating member tip, each can function as a "safety member" upon penetration of the safety penetrating instrument into an anatomical cavity. The cannula, whether or not it functions as a safety member, can be a portal sleeve, a needle open at both ends with fluid flow therethrough, a catheter or any other tubular component of a medical instrument. When the cannula is not triggered to protrude as a safety member, it is coupled with a safety member such as a tubular safety shield disposed between the cannula and penetrating member, a safety probe fitted within the penetrating member, or a component partly within and around the penetrating member and movable to protrude relative to the penetrating member to protect the distal end thereof when triggered. On the other hand, if the cannula does function as a safety member, it can be coupled with a protective sheath or probe that is not triggered to protrude or with any of the aforementioned safety members.

The safety penetrating instrument of the present invention is also advantageous in that the force for extending the safety members to protrude beyond the tip of the penetrating member does not have to be overcome during penetration of the cavity wall, thereby minimizing the force to penetrate required. Hence, the extending force for biasing the safety member (whether it be the cannula, a safety shield or probe, or both) to the safety member extended position can be relatively strong to assure protrusion of the safety member even should the safety member engage tissue in the anatomical cavity wall or within the anatomical cavity or should any tissue be jammed between one of the safety members and the penetrating member or both safety members. The strong distal bias toward the safety member extended position provides the surgeon with the psychological benefit of knowing the safety member is protecting the penetrating member and provides an easily felt tactile signal that the safety member has moved to the safety member extended position for confirmation of penetration. Movement of one or both safety members to safety member extended positions can also be confirmed visually by noticing the movement of handles connected with the respective safety members and the penetrating member, such as handles 88 and 90. Moreover, should tissue within the anatomical cavity be contacted by the distal end of the safety members, those safety members mounted on bias members will bounce or give a little in the nature of a shock absorber to protect such contacted tissue.

As mentioned previously, various mechanisms can be employed to produce the locking and releasing functions of the present invention, such as, for example, multiple movably or pivotally mounted cams or pawls. When separate latches are used for locking the penetrating member and safety members prior to use, any combination of the members can be locked or left unlocked by selectively operating appropriate handles together or on an individual basis. For example, if the handle connecting the penetrating member is operated to lock the penetrating member in the penetrating member extended position, the handles connecting respective safety members may or may not be operated to lock one or both safety members in the safety member retracted position. If both safety member handles are not operated, the safety members will not be triggered to protrude and the safety penetrating instrument will function as a retractable safety penetrating instrument only.

It will also be appreciated that the locking and releasing mechanisms can be arranged in the housing and/or the hub or within the penetrating member in many various ways to minimize the length of the housing and/or the hub and, therefore, the overall length of the safety penetrating instruments. For example, in the modified penetrating unit illustrated in FIG. 68, the retracting and extending members are disposed coaxially within the penetrating member and safety member, respectively, to reduce the overall length of the hub, and latches for locking the safety member and penetrating member are coupled to achieve substantially simultaneous retraction of the penetrating member and extension of the safety member in response to penetration of the penetrating member into an anatomical cavity.

The modified penetrating unit 2914 is similar to penetrating unit 14 and includes a penetrating member 2920, a safety member 2922 in the form of a tubular safety shield surrounding the penetrating member 2920, and a hub 2924 mounting proximal ends of the penetrating member 2920 and safety shield 2922. The hub 2924 includes forward and rear walls 2941 and 2944 (the spacing between which defines the "length" of the hub) and an inner wall 2956 extending transversely or perpendicular to the longitudinal axis of the penetrating member 2920 intermediate the front and rear walls 2941 and 2944. A tubular guide member 2942 has a proximal end mounted around an opening formed in the inner wall 2956 and terminates distally in an annular distal face 2929 defining a somewhat smaller opening for passage of the penetrating member 2920. An annular flange 2927 is formed on an inner surface of the guide member 2942 and proximally spaced from the distal end 2929 thereof to maintain an annular space between the penetrating member 2920 and the guide member 2942 and to serve as a proximal face.

The penetrating member 2920 includes a body 2923 configured to pass through the openings defined in the proximal and distal faces 2964 and 2929 of the guide member 2942, and a penetrating tip 2921 secured to the distal end of the body 2923 and configured to fit telescopically within the tubular safety shield 2922. The penetrating member body 2923 terminates proximally in a transverse flange 2940 disposed proximally of the inner wall 2956 of the hub 2924. A collar 2950, shown as a washer, is disposed around the body 2923 between the inner wall 2956 and the penetrating member flange 2940. A retracting member 2954, in the form of a helical spring, is coiled around the penetrating member body 2923 and held in compression between the guide member flange 2927 and the collar 2950. A bias member 2952, shown as a helical coil spring, is held in compression between the penetrating tip 2921 of the penetrating member 2920 and the distal face 2929 of the guide member to bias the penetrating tip 2921 distally while allowing a predetermined amount of proximal movement during penetration of the anatomical cavity wall.

The safety shield 2922 is similar to safety shield 22, terminating proximally in a transverse flange 2964, but also includes an internal flange 2925 spaced distally of the transverse flange 2964 and defining an opening for passage of the guide member 2942 therethrough. An extending member 2974, in the form of a helical spring, is coiled around the guide member 2942 and held in compression between the safety shield inner flange 2925 and the hub inner wall 2956 to move the safety shield 2922 from a retracted position illustrated by phantom lines to the extended position shown with solid lines.

A first latch 2980 is mounted on a pin 2981 secured to the rear wall 2944 of the hub 2924 and extends distally toward an off-axis opening 2957 formed in the hub inner wall 2956. The latch 2980 includes a distally expanding wedge-shaped body 2983 carrying a trigger lever 2986 and terminating in shoulders 2982 and 2979 connecting a short neck 2985. The shoulder 2982 faces the penetrating member 2920 and serves as a pawl for preventing proximal movement of the collar 2950 when the penetrating member is in the extended position. Like trigger lever 86, trigger lever 2986 is a generally L-shaped lever mounted centrally on a pin 2989 secured to the latch body 2983 and having a pair of trigger legs 2991 and 2995; however, horizontal trigger leg 2991 extends proximally, rather than distally, from pin 2989 and a leaf spring 2993 is connected between the latch body 2983 and the leg 2991 to bias the trigger lever 2986 counterclockwise looking at FIG. 68 while preventing rotation beyond a certain point.

A second latch 2980' is rotatably mounted on a pin 2981' secured to the front wall 2941 of the hub 2924 and extends proximally toward the first latch 2980. The second latch 2980' also includes a tapered body 2983' and terminates proximally in a shoulder or pawl 2984' connecting a short neck 2985' that engages the neck 2985 of latch 2980 on the side opposite shoulder pawl 2982. A leaf spring 2903 is connected between a side wall of the hub 2924 and the latch body 2983' to bias the latch 2980' counterclockwise and thus the latch 2980 clockwise looking at FIG. 68. A locking element 2901 in the form of a ramped protrusion is also shown in phantom being carried at a distal end of latch body 2983' for locking the safety shield in the extended position and may be released, for example, by positioning a control button such as control button 389 adjacent latch 2980' to induce rotation thereof when the button is depressed.

Figure 68:
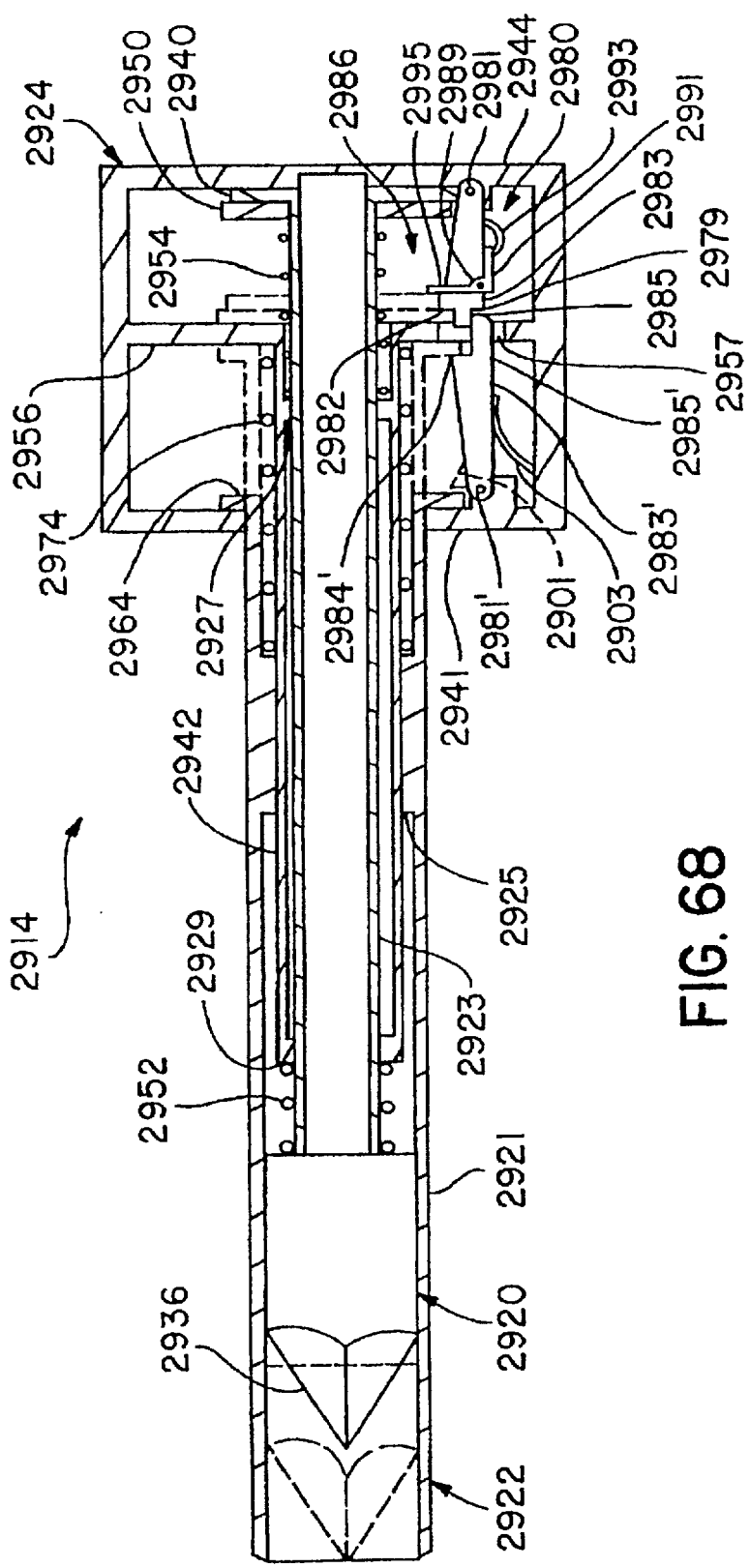
FIG. 68 is a side view, partly in section, showing a modified penetrating unit for use in the safety penetrating instrument of the present invention.

In use, the penetrating unit 2914 is provided as shown in FIG. 68 and is coupled with any suitable portal unit with or without triggered protrusion of the portal sleeve. Handles, such as handles 88 and 90, are drawn together to extend the penetrating member 2920 and to retract the safety shield 2922 into the positions shown in phantom whereupon the penetrating member collar 2950 and safety shield flange 2964 are locked in place by latches 2980 and 2980', respectively. With the penetrating member 2920 extended and the safety shield 2922 retracted, the safety penetrating instrument can be used to penetrate an anatomical cavity wall (not shown). During penetration, the penetrating member penetrating tip 2921 is permitted to move proximally against the bias of spring 2952 thereby moving the penetrating member body 2923 and flange 2940 proximally. Proximal movement of the penetrating member flange 2940 against leg 2995 of trigger lever 2986 causes the lever to rotate clockwise looking at FIG. 68 against the bias of leaf spring 2993. When the penetrating member flange 2940 moves further proximally to be disposed proximally of the trigger leg 2995, the lever 2986 springs back to the position shown to present a distal surface for engaging the penetrating member flange 2940 on its return trip under the distal bias of spring 2952. Upon penetrating into the anatomical cavity, the penetrating member tip 2921 springs distally forward carrying the penetrating member body 2923 and flange 2940 distally forward. The penetrating member flange 2940 bears against the trigger leg 2995, which is restrained from rotating counterclockwise, thus creating a moment to rotate the entire latch 2980 counterclockwise. Counterclockwise rotation of latch 2980 releases the penetrating member collar 2950 while simultaneously causing neck 2985 to bear against neck 2985' of latch 2980', thereby inducing clockwise rotation of latch 2980' away from safety shield flange 2964. Release of latches 2980 and 2980' permits retracting member 2954 to drive the collar 2950 and thus penetrating member flange 2940 proximally into abutment with the rear wall 2944 of the hub 2924, and permits extending member 2974 to drive the safety shield internal flange 2925 distally until safety shield proximal flange 2964 abuts the front wall 2941 of the hub 2924. This combination of movements places the penetrating member distal end 2936 in a protected position proximally spaced from the safety shield distal end 2962, allowing the penetrating unit 2914 to be removed from the portal unit and procedures to be performed through the lumen of the portal sleeve.

Various other locking and releasing mechanisms that can be used in the safety penetrating instruments of the present invention are disclosed in applicant's prior applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868, 566 and Ser. No. 07/868,578, filed Apr. 15, 1992, Ser. No. 07/929,338, filed Aug. 14, 1992, Ser. No. 07/845,177, filed Sep. 15, 1992, Ser. No. 07/945,177, filed Sep. 14, 1992, Ser. No. 08/079,586, filed Jun. 22, 1993, Ser. No. 08/195,512, filed Feb. 14, 1994, Ser. No. 08/196,029, filed Feb. 14, 1994, Ser. No. 08/196,027, filed Feb. 14, 1994, Ser. No. 08/195, 178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference. The above applications disclose automatically retracting safety penetrating instruments such that modification of the locking and releasing mechanisms requires configuring the latches for locking the penetrating member in an extended position and the cannula and/or a separate safety member in retracted positions. If a latch is provided carrying a trigger lever, it can be mounted as part of the portal unit or the penetrating unit allowing the triggering mechanism to remain in place with the portal unit or to be withdrawn with the penetrating unit, respectively. Further, where a single latch holds a member (e.g., the penetrating member, cannula, or safety shield) and is responsive to movement of that member to be released, a separate mechanism can also be provided to release the latch in response to movement of one or both of the other members to achieve redundant triggering, or a separate mechanism can be provided to lock and release the member and/or the latch holding the member in response to movement of one or both of the other members to achieve redundant locking.

In any safety penetrating instrument having a latch biased to engage one of the members, a control button such as control button 389 can be located adjacent the latch and be manually operable to release the latch from engaging the member. Also, any of the foregoing safety penetrating instruments can be provided with locking elements such as locking elements 1301 or 1302 to engage and lock the penetrating member and/or any safety members when the safety penetrating instrument moves to the protective state.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in a wall of an anatomical cavity comprising
    a housing;
    a cannula mounted by said housing and having a distal end for positioning within the anatomical cavity, a proximal end for positioning externally of the anatomical cavity wall and a lumen extending between said distal and proximal ends of said cannula;
    a penetrating member disposed in said cannula and having a distal end for penetrating the anatomical cavity wall;
    a protective sheath disposed between said penetrating member and said cannula;
    retracting means for moving said penetrating member proximally relative to said housing from a penetrating member extended position to a penetrating member retracted position;
    extending means for moving said cannula distally relative to said housing from a cannula retracted position exposing said penetrating member distal end to a cannula extended position protecting said penetrating member distal end;
    locking means for locking said penetrating member in said penetrating member extended position and said cannula in said cannula retracted position to prevent distal movement of said cannula relative to said housing beyond said cannula retracted position; and
    releasing means responsive to entry of said safety penetrating instrument into the anatomical cavity for triggering release of said locking means to permit said retracting means to move said penetrating member proximally relative to said housing from said penetrating member extended position to said penetrating member retracted position and to permit said extending means to move said cannula distally relative to said housing from said cannula retracted position to said cannula extended position to cover and protect said distal end of said penetrating member.

2. A safety penetrating instrument as recited in claim 1 wherein said penetrating member distal end includes a tapered portion and further comprising bias means for biasing said cannula, said penetrating member and said protective sheath distally during penetration to maintain alignment of said distal ends of said cannula and said protective sheath with a proximal end of said tapered portion of said penetrating member.

3. A safety penetrating instrument as recited in claim 1 wherein said retracting means includes means for moving said penetrating member and said protective sheath proximally relative to said housing from respective extended positions to respective retracted positions, said locking means includes means for locking said penetrating member and said protective sheath in said respective extended positions, and said releasing means includes means responsive to entry of said safety penetrating instrument into the anatomical cavity for triggering release of said locking means to permit said retracting means to move said penetrating member and said protective sheath proximally relative to said housing from said respective extended positions to said respective retracted positions and to permit said extending means to move said cannula distally relative to said housing from said cannula retracted position to said cannula extended position to cover and protect said distal end of said penetrating member.

4. A safety penetrating instrument as recited in claim 3 wherein said locking means includes a first latch engaging said cannula to prevent extension thereof and a second latch engaging said penetrating member and said protective sheath to prevent retraction thereof and wherein said releasing means includes a first trigger responsive to entry of said cannula into the anatomical cavity to release said first latch and a second trigger responsive to entry of at least one of said penetrating member and said protective sheath to release said second latch.

5. A safety penetrating instrument for establishing a portal in a wall of an anatomical cavity comprising
    a housing;
    a cannula mounted by said housing and having a distal end for positioning within the anatomical cavity, a proximal end for positioning externally of the anatomical cavity wall and a lumen extending between said distal and proximal ends of said cannula;
    a penetrating member disposed in said cannula and having a distal end for penetrating the anatomical cavity wall;
    retracting means for moving said penetrating member proximally relative to said housing from a penetrating member extended position to a penetrating member retracted position;

a protective sheath disposed proximate said penetrating member to cover said penetrating member distal end when said penetrating member is in said penetrating member retracted position;

extending means for moving said cannula distally relative to said housing from a cannula retracted position to a cannula extended position protecting said distal end of said penetrating member;

locking means for locking said penetrating member in said penetrating member extended position and said cannula in said cannula retracted position to prevent distal movement of said cannula relative to said housing beyond said cannula retracted position; and releasing means responsive to entry of said safety penetrating instrument into the anatomical cavity for triggering release of said locking means to permit said retracting means to move said penetrating member proximally relative to said housing from said penetrating member extended position to said penetrating member retracted position and to permit said extending means to move said cannula distally relative to said housing from said cannula retracted position to said cannula extended position to protect said distal end of said penetrating member within the anatomical cavity.

6. A safety penetrating instrument as recited in claim 5 wherein said penetrating member includes a proximal end and said protective sheath includes a proximal end and further comprising a housing mounting said proximal end of said cannula and a hub mounting said proximal ends of said penetrating member and said protective sheath.

7. A safety penetrating instrument as recited in claim 6 wherein said releasing means is responsive to entry of said protective sheath into the anatomical cavity.

8. A safety penetrating instrument as recited in claim 6 wherein said releasing means is responsive to entry of said cannula into the anatomical cavity.

9. A safety penetrating instrument as recited in claim 6 wherein said releasing means is responsive to entry of said penetrating member into the anatomical cavity.

10. A safety penetrating instrument as recited in claim 6 wherein said releasing means is responsive to entry of said protective sheath and cannula into the anatomical cavity.

11. A safety penetrating instrument as recited in claim 6 wherein said releasing means is responsive to entry of said protective sheath and penetrating member into the anatomical cavity.

12. A safety penetrating instrument as recited in claim 6 wherein said releasing means is responsive to entry of said cannula and penetrating member into the anatomical cavity.

13. A safety penetrating instrument as recited in claim 6 wherein said releasing means is responsive to entry of said protective sheath, cannula and penetrating member into the anatomical cavity.

* * * * *